(12) United States Patent
Leonard et al.

(10) Patent No.: US 11,583,650 B2
(45) Date of Patent: Feb. 21, 2023

(54) VARIABLE GEOMETRY CANNULA

(71) Applicant: Vapotherm, Inc., Exeter, NH (US)

(72) Inventors: Scott A. Leonard, Bedford, NH (US); Amber Fuchs, Exeter, NH (US)

(73) Assignee: VAPOTHERM, INC., Exeter, NH (US)

( * ) Notice: Subject to any disclaimer, the term of this patent is extended or adjusted under 35 U.S.C. 154(b) by 245 days.

(21) Appl. No.: 16/912,095

(22) Filed: Jun. 25, 2020

(65) Prior Publication Data
US 2020/0405991 A1     Dec. 31, 2020

Related U.S. Application Data

(60) Provisional application No. 62/868,376, filed on Jun. 28, 2019.

(51) Int. Cl.
*A61M 16/06*     (2006.01)

(52) U.S. Cl.
CPC .............. *A61M 16/0666* (2013.01)

(58) Field of Classification Search
CPC ................................. A61M 16/0666
USPC ..................................... 127/207.18
See application file for complete search history.

(56) References Cited

U.S. PATENT DOCUMENTS

| | | | | |
|---|---|---|---|---|
| RE24,534 E | * | 9/1958 | Dahl ............... | G05D 7/012 239/533.14 |
| 2,941,544 A | * | 6/1960 | Peras ............... | G05D 7/012 137/859 |
| 4,003,398 A | * | 1/1977 | Duveau ............ | F16K 15/147 137/493 |
| 4,422,456 A | | 12/1983 | Tiep | |
| 4,708,166 A | * | 11/1987 | Kobold ............ | G05D 7/0113 137/859 |
| 4,782,832 A | | 11/1988 | Trimble et al. | |

(Continued)

FOREIGN PATENT DOCUMENTS

| AU | 2013212314 | 11/2017 |
|---|---|---|
| AU | 2013337995 | 6/2018 |

(Continued)

OTHER PUBLICATIONS

Doshi et al., "High-Velocity Nasal Insufflation in the Treatment of Respiratory Failure: A Randomized Clinical Trial", Annals of Emergency Medicine, Jul. 2017;72(1):73-83.

(Continued)

*Primary Examiner* — Craig M Schneider
*Assistant Examiner* — David R Deal
(74) *Attorney, Agent, or Firm* — McDermott Will & Emery LLP

(57) ABSTRACT

A cannula for providing respiratory therapy to a patient includes a first nasal prong having a proximal end attached to a cannula body and a distal end for insertion into a nare of the patient. The first nasal prong defines a lumen for a flow of breathing gas from a source of breathing gas to the nare of the patient, and the first nasal prong has a variable geometry such that a cross-sectional area of the lumen at the distal end of the first nasal prong varies with a flow rate of the breathing gas. Varying the cross-sectional area of the first nasal prong lumen with the flow rate of the breathing gas enables the first nasal prong to maintain a high velocity flow to the nare for effective flushing of the patient's airway.

19 Claims, 11 Drawing Sheets

(56) References Cited

U.S. PATENT DOCUMENTS

| | | | |
|---|---|---|---|
| 4,790,308 A | | 12/1988 | Weichselbaum |
| 5,099,836 A | | 3/1992 | Rowland et al. |
| 5,113,911 A | * | 5/1992 | Hirsh .................. A61M 39/22 |
| | | | 137/844 |
| 5,433,242 A | * | 7/1995 | Buchtel .................. B67D 7/74 |
| | | | 222/481.5 |
| 6,561,188 B1 | * | 5/2003 | Ellis .................. A61M 16/107 |
| | | | 128/207.18 |
| 6,805,126 B2 | | 10/2004 | Dutkiewicz |
| 6,986,353 B2 | | 1/2006 | Wright |
| 7,007,694 B2 | | 3/2006 | Aylsworth et al. |
| 7,481,244 B2 | * | 1/2009 | Bivin .................. G05D 7/0173 |
| | | | 366/337 |
| 7,662,181 B2 | * | 2/2010 | Deem .................. F16K 15/147 |
| | | | 623/9 |
| 7,743,770 B2 | | 6/2010 | Curti et al. |
| 7,832,400 B2 | | 11/2010 | Curt et al. |
| 9,333,317 B2 | | 5/2016 | Cortez, Jr. et al. |
| 9,597,263 B2 | * | 3/2017 | Visveshwara ....... A61J 15/0003 |
| 9,822,515 B2 | * | 11/2017 | Wu .................. G05D 7/012 |
| 9,925,348 B2 | | 3/2018 | Payton et al. |
| 10,100,622 B2 | * | 10/2018 | Gonzalez ................ E21B 43/12 |
| 10,265,494 B2 | | 4/2019 | Vapotherm |
| 10,300,236 B2 | | 5/2019 | Vapotherm |
| 2004/0112383 A1 | | 6/2004 | Curt et al. |
| 2004/0226566 A1 | | 11/2004 | Gunaratnam et al. |
| 2005/0028822 A1 | | 2/2005 | Sleeper et al. |
| 2005/0066976 A1 | | 3/2005 | Wondka |
| 2005/0103347 A1 | | 5/2005 | Curt et al. |
| 2005/0229927 A1 | | 10/2005 | Fink et al. |
| 2005/0229928 A1 | | 10/2005 | Irvi |
| 2006/0030696 A1 | | 2/2006 | Bonnerjea et al. |
| 2006/0230929 A1 | | 10/2006 | Bliss et al. |
| 2006/0230931 A1 | | 10/2006 | Bliss et al. |
| 2007/0175473 A1 | | 8/2007 | Lewis et al. |
| 2008/0121230 A1 | | 5/2008 | Cortez et al. |
| 2008/0223375 A1 | | 9/2008 | Cortez et al. |
| 2009/0044808 A1 | | 2/2009 | Guney et al. |
| 2009/0101147 A1 | | 4/2009 | Landis et al. |
| 2009/0250132 A1 | * | 10/2009 | Bivin .................. G05D 7/0186 |
| | | | 138/45 |
| 2009/0253995 A1 | | 10/2009 | Lewis et al. |
| 2010/0096019 A1 | * | 4/2010 | DiPerna .................. F15D 1/00 |
| | | | 137/13 |
| 2010/0108073 A1 | | 5/2010 | Zollinger et al. |
| 2010/0113955 A1 | | 5/2010 | Colman et al. |
| 2010/0252037 A1 | | 10/2010 | Wondka et al. |
| 2010/0282247 A1 | | 11/2010 | Kadrichu et al. |
| 2011/0067704 A1 | | 3/2011 | Kooij et al. |
| 2011/0073116 A1 | * | 3/2011 | Genger .............. A61M 16/0677 |
| | | | 128/207.18 |
| 2011/0094518 A1 | | 4/2011 | Cipollone et al. |
| 2011/0146685 A1 | | 6/2011 | Allan et al. |
| 2011/0232649 A1 | | 9/2011 | Collazo et al. |
| 2011/0284001 A1 | | 11/2011 | Tero |
| 2012/0090622 A1 | | 4/2012 | Chang |
| 2012/0125332 A1 | | 5/2012 | Niland et al. |
| 2012/0167878 A1 | | 7/2012 | Belson et al. |
| 2012/0304992 A1 | | 12/2012 | Ratto et al. |
| 2013/0008447 A1 | | 1/2013 | Gunaratnam et al. |
| 2013/0092165 A1 | | 4/2013 | Wondka |
| 2013/0152925 A1 | | 6/2013 | Rahmel et al. |
| 2013/0160772 A1 | | 6/2013 | Tabrizchi |
| 2014/0066801 A1 | | 3/2014 | Tero |
| 2014/0116447 A1 | | 5/2014 | Cortez, Jr. et al. |
| 2014/0137744 A1 | | 5/2014 | Wilkinson et al. |
| 2014/0147506 A1 | | 5/2014 | Longest et al. |
| 2014/0150789 A1 | | 6/2014 | Flanagan et al. |
| 2014/0158127 A1 | | 6/2014 | Boucher et al. |
| 2014/0166009 A1 | | 6/2014 | Flanagan et al. |
| 2014/0230942 A1 | * | 8/2014 | Takai .................. B60H 1/3442 |
| | | | 138/45 |
| 2014/0261704 A1 | | 9/2014 | Hoogenakker et al. |
| 2014/0366885 A1 | | 12/2014 | Haibach et al. |
| 2015/0000654 A1 | | 1/2015 | Martin |
| 2015/0000659 A1 | | 1/2015 | Martin |
| 2015/0000660 A1 | | 1/2015 | Martin |
| 2015/0090255 A1 | | 4/2015 | Gulliver et al. |
| 2015/0230731 A1 | | 8/2015 | Levitsky et al. |
| 2016/0015296 A1 | | 1/2016 | Garaycochea |
| 2016/0015921 A1 | | 1/2016 | Harrison et al. |
| 2016/0030696 A1 | * | 2/2016 | Klenner .............. A61M 16/0683 |
| | | | 128/207.18 |
| 2016/0158476 A1 | | 6/2016 | Tatkov |
| 2016/0271353 A1 | * | 9/2016 | Cheung .............. A61M 16/0666 |
| 2017/0000965 A1 | | 1/2017 | Cortez, Jr. et al. |
| 2019/0328990 A1 | | 10/2019 | Cortez et al. |
| 2019/0328993 A1 | | 10/2019 | Cortez et al. |

FOREIGN PATENT DOCUMENTS

| | | |
|---|---|---|
| AU | 2017251790 | 3/2020 |
| EP | 2022528 A2 | 2/2009 |
| EP | 2247331 A1 | 11/2010 |
| EP | 2806926 | 5/2017 |
| EP | 2914322 | 12/2018 |
| EP | 3646913 | 5/2020 |
| EP | 3216475 | 7/2020 |
| EP | 3747488 | 12/2020 |
| FR | 2827778 A1 | 1/2003 |
| WO | WO-9818513 | 5/1998 |
| WO | WO-2006138579 | 12/2006 |
| WO | WO-2008060587 A2 | 5/2008 |
| WO | WO-2013041996 A2 | 3/2013 |
| WO | WO-2013042004 A1 | 3/2013 |
| WO | WO-2013112545 | 8/2013 |
| WO | WO-2013157960 A1 | 10/2013 |
| WO | WO-2014070833 | 5/2014 |
| WO | WO-2014142681 A1 | 9/2014 |
| WO | WO-2015121815 A1 | 8/2015 |
| WO | WO-2015164921 A1 | 11/2015 |
| WO | WO-2016043607 A1 | 3/2016 |
| WO | WO-2017062677 | 4/2017 |
| WO | WO-2018005851 A1 | 1/2018 |
| WO | WO-2018065588 | 4/2018 |
| WO | WO-2018068085 | 4/2018 |
| WO | WO-2019191814 | 10/2019 |

OTHER PUBLICATIONS

Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).

International Search Report dated Dec. 3, 2018, Application No. PCT/US2018/049979 (9 pages).

International Search Report dated Oct. 18, 2017, Application No. PCT/US2017/040079 (21 pages).

International Search Report dated Oct. 4, 2016, Application No. PCT/US2016/040465 (16 pages).

International Search Report dated Oct. 7, 2020, Application No. PCT/US2020/039641 (13 pages).

* cited by examiner

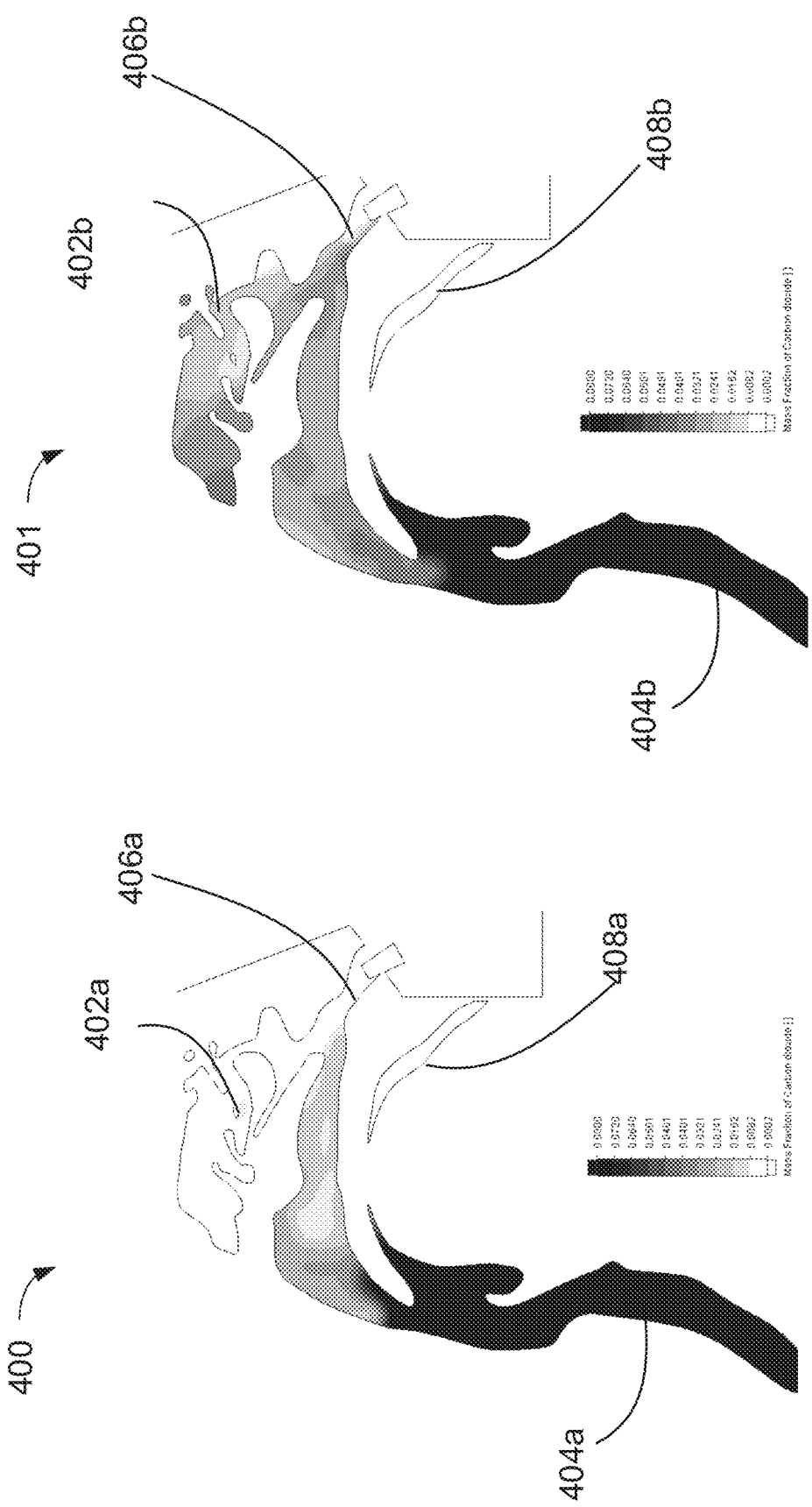

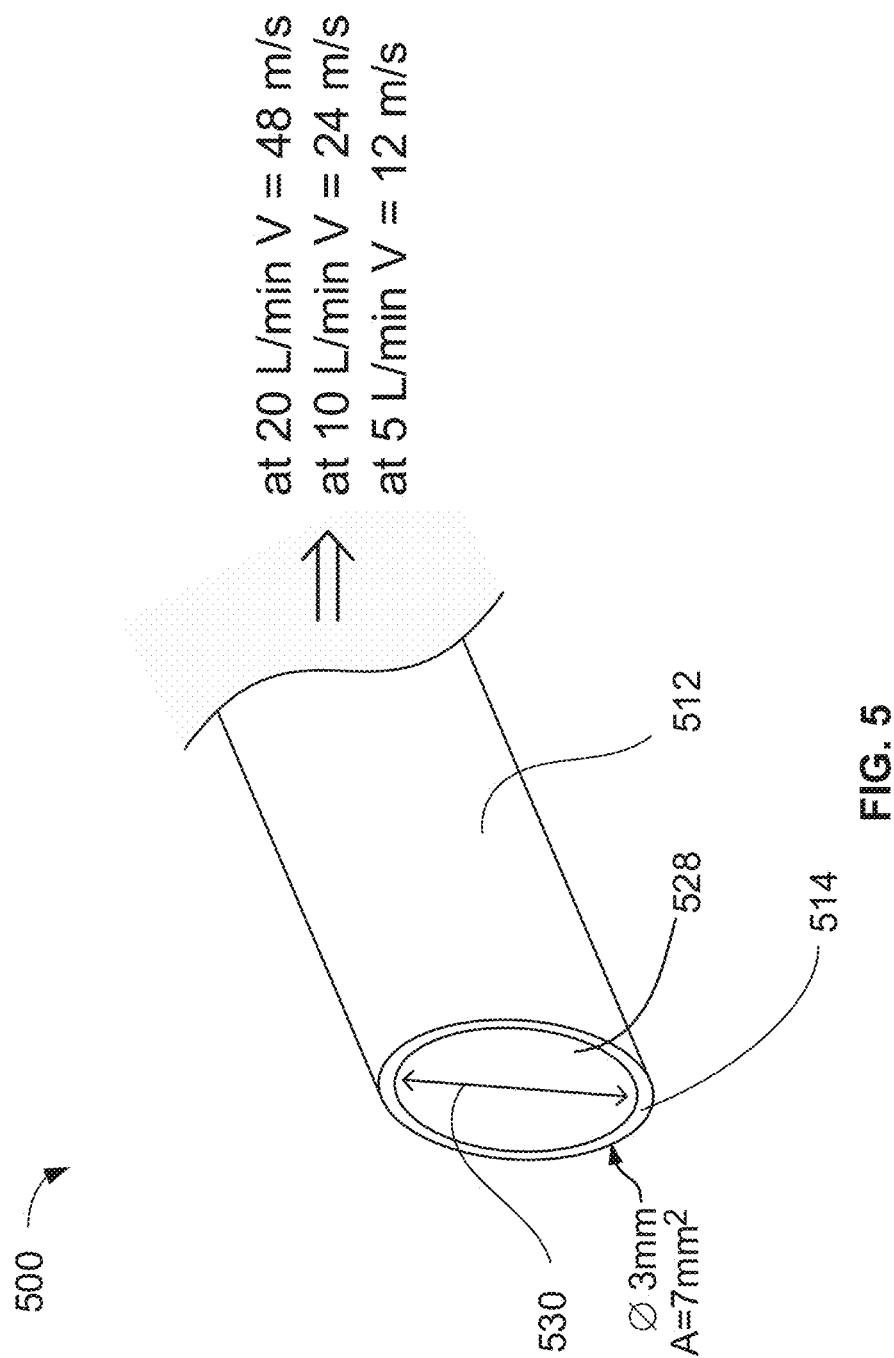

VARIABLE GEOMETRY CANNULA

CROSS-REFERENCE TO RELATED APPLICATIONS

This application claims priority to and the benefit of U.S. Provisional Patent Application No. 62/868,376, filed on Jun. 28, 2019, and entitled "VARIABLE GEOMETRY CANNULA", the entire contents of which is incorporated herein by reference.

BACKGROUND

A single prong cannula can be used to provide respiratory therapy in a comfortable manner. The single prong cannula can also efficiently flush the airways through the non-obstructed nare. However, the flow velocity provided by the single prong cannula must be maintained at a high enough level to adequately flush the nasopharyngeal dead space to eject $CO_2$ from the patient's breathing passages and prevent re-inhalation of $CO_2$. Providing breathing gas at a low volumetric flow rate may be desirable for patient comfort, as a low flow rate will have reduced noise, or may be necessary in non-hospital settings where high flow rate breathing gas is not readily available. As the volumetric flow rate is decreased, however, the velocity of the gas provided to the patient through a conventional nasal prong is also decreased, lowering the ability of the breathing gas to flush the airways of the patient.

In terms of respiratory fluid dynamics, the volumetric flow rate of a breathing gas is proportional to the velocity of the gas and the area of the passageway through which the gas flows. When a cannula is sized properly for its maximum flow rate the opening at the nare must be sized large enough to maintain a reasonable pressure drop and not generate too high a velocity of gas flow so as to be dangerous or unpleasant to the patient. But when the cannula is operated at lower volumetric flow rates the velocity falls and can cause suboptimal flush to the upper airway. Traditionally, this dependence of the flow velocity on the flow rate of the gas dictates a required flow rate, or can be overcome by changing a size of the cannula used by the patient, which can be costly and confusing to the patient or clinician.

Variation in volumetric flow rate can be unpredictable and variable, depending on the facility and the patients. Accordingly, there is a necessity for development of a single prong cannula that can be utilized to provide a breathing gas to a patient at a constant velocity even when the breathing gas is provided at various gas flow rates.

SUMMARY

Disclosed herein are approaches for addressing the problems and shortcomings of the state of the art, as identified above. The devices and methods described herein thus enable the delivery of breathing gas to a patient through nasal cannulas having variable geometry prongs to provide effective flush of the patient's airways. Flush is generally improved by increasing the energy of the breathing gas flow, which can be done by, for example, maintaining a high velocity or introducing turbulence in the flow. Accordingly, certain features provided herein maintain a high velocity of breathing gas flow or introduce turbulence into the breathing gas flow. More particularly, disclosed herein are nasal cannulas having one or more prongs with variable geometry and/or protrusions for providing respiratory therapy at constant velocity, despite variations in the flow rate of the breathing gas, or with added turbulence.

Nasal cannulas as referenced herein can allow the delivery of high velocity breathing gas, in a constant manner, at variable flow rates. In one aspect, a variable geometry cannula includes a first nasal prong having a proximal end attached to a cannula body and a distal end for insertion into a nare of the patient. The first nasal prong defines a lumen for a flow of breathing gas from a source of breathing gas to the nare of the patient, and the first nasal prong has a variable geometry such that a cross-sectional area of the lumen at the distal end of the first nasal prong varies with a flow rate of the breathing gas.

In certain implementations, the cross-sectional area of the lumen at the distal end of the first nasal prong may be designed to increase with an increase in flow rate and decrease with a decrease in flow rate. The variations in cross-sectional area of the lumen may be designed to minimize a reduction in flow velocity of breathing gas at low flow rates compared to the reduction in flow velocity of breathing gas flowing in a nasal prong with a constant cross-sectional area. The distal end of the first nasal prong may be designed to change between a first expanded shape and a second folded shape, such that a cross-sectional area of the second folded shape is smaller than a cross-sectional area of the first expanded area. The flow velocity through the first nasal prong may be about the same in the first expanded shape as in the second folded shape. The first expanded shape and the second folded shape may be formed as any of a variety of geometric shapes.

For example, the first expanded shape comprises a regular polygon, such as a decagon, an octagon, or a hexagon at a first flow rate, and the second folded shape comprises a star having a number of points, such as a five-pointed star, a four-pointed star, or a three-pointed star at a second flow rate. In some implementations, the distal end of the first cannula is further configured to assume a third folded shape at a third flow rate, where the third flow rate is less than the first or second flow rates, the third folded shape having a third cross-sectional area less than the second cross-sectional area. In some implementations, the distal end of the first nasal prong is shaped as a dome having a plurality of slits, and wherein at no flow through the first nasal prong the slits are configured to be closed and at a first flow rate through the first nasal prong the slits are configured to be open.

In some implementations, the first expanded shape comprises a circular cross-sectional shape at the first flow rate, the circular shape having a first distance extending between a first point and a second point opposite the first point on a circumference of the circular shape, and a second distance extending between a third point and a fourth point opposite the third point, wherein the third point is equidistant from the first point and the second point, and wherein at a first flow rate of breathing gas flow through the first nasal prong a first difference between the first distance and the second distance is less than a second difference between the first distance and the second distance at a second flow rate of breathing gas lower than the first flow rate. At the second flow rate, the cross-sectional shape of the distal end of the first nasal prong may comprise any one of: an oval shape, a hippopede or pinched oval shape, a double-pointed teardrop shape and crescent/kidney shape.

In certain implementations, the first nasal prong may be formed from a shape memory material, and the cross-sectional area of the lumen at the distal end of the first nasal prong may be designed to change in response to an environmental stimuli. In certain implementations, the first nasal prong may be formed from piezoelectric materials and the cross-sectional area of the lumen at the distal end of the first nasal prong may be designed to change in response to the application of an electrical signal.

In certain implementations, the first nasal prong may include an occluding nasal pillow formed by material extending from an external surface of the first nasal prong, for example extending orthogonally from the external surface. The nasal pillow may substantially circumscribe the first nasal prong. The nasal pillow may be sized to occlude a space between the nare and the first nasal prong when the first nasal prong is positioned in the nare of the patient. The nasal pillow may be a deformable material and may be formed as a rounded dome or any other shape designed to maximize patient comfort while occluding the patient's nare around the first nasal prong or otherwise. In certain implementations, the nasal cannula may include a second nasal prong which does not include an occluding nasal pillow extending orthogonally from an external surface and does not include a lumen. The second nasal prong may aid in stabilizing the cannula on a patient's face.

In certain implementations, the first nasal prong may include one or more internal protrusions positioned within the lumen of the first nasal prong. In some implementations the internal protrusions are shaped as a rectangle or a chevron protruding from a sidewall within the lumen of the first nasal prong. The protrusions may be positioned within the lumen to minimize a reduction in flow velocity of the breathing gas at low flow rates compared to nasal prongs with smooth interior lumens. In some implementations, the one or more internal protrusions is shaped as a rectangular surface protruding from the sidewall within the lumen into a gas flow path of the first nasal prong. The rectangular surface may be angled from an axis collinear with a longitudinal axis extending from the proximal end to the distal end of the first nasal prong; for example, the rectangular surface is angled 45° or less from the axis collinear with the longitudinal axis, or the rectangular surface is angled more than 45° from the axis collinear with the longitudinal axis. In some implementations, the one or more internal protrusions is shaped as a chevron, the chevron including a point and two angled arms extending from the point. For example, the point is oriented toward the proximal end or the distal end of the first nasal prong. Protrusions positioned within the first nasal prong provide at least an advantage of introducing turbulence into the breathing gas flow, in order to increase the energy of the flow and provide more effective flush of the patient's airway.

In some implementations, the first nasal prong is formed from a polymer. The first nasal prong may be formed by injection molding, liquid silicone molding, or dip molding. The first nasal prong may further include one or more longitudinal fold lines extending along a longitudinal length along the first nasal prong.

In another aspect there is provided a method for manufacturing a nasal cannula for respiratory therapy which includes a nasal cannula having a cannula body including a first nasal prong having a proximal end attached to a cannula body, and a variable-geometry distal end for insertion into a nare of the patient. Embodiments of cannula manufactured by the method are disclosed herein. The manufacturing method uses a mandrel having a first end, a second end, and protrusions extending from the first end toward the second end. The method includes coating the mandrel with a material, curing the coated mandrel, trimming the coated mandrel to create an opening in the coating of the trimmed mandrel, and removing the cured coating from the mandrel. The protrusions extending from the first end toward the second end result in areas having a thinner cured coating such that the cured coating is more flexible and able to bend or fold at the areas having the thinner cured coating. The areas having thinner cured coating may be configured as lines extending parallel to a longitudinal axis of the mandrel from the first end toward the second end.

In some implementations, the coating step includes immersing the mandrel into the material and removing the mandrel from the material. The mandrel may include at least one shaped indentation in a side of the mandrel. The mandrel may include a ring shaped protrusion circumscribing the mandrel, the ring shaped protrusion extending a distance from a surface of the mandrel configured to fit the nare of the patient.

In another aspect, there is provided a method of providing respiratory therapy to a patient which includes receiving a first flow of breathing gas at a first inlet end of a lumen of a cannula body, and receiving a second flow of breathing gas at a second inlet end of the lumen of the cannula body opposite the first inlet end. The lumen of the cannula body is continuous between the first inlet end and the second inlet end. The method may also include delivering the first and second flows of breathing gas through a nasal prong extending from an outer surface of the cannula body. The nasal prong may include a lumen extending from the lumen of the cannula body to a distal end of the nasal prong, and the distal end of the nasal prong is sized to be inserted into a nare of a patient. The volumetric flow rate through the nasal prong from the combined first and second flows of breathing gas is lower than (e.g., about half) the volumetric flow rate through both prongs of a conventional two prong cannula, such that the combined first and second flows of breathing gas is delivered to the patient at a velocity that is the about the same as the velocity at which breathing gas is delivered to the patient via the one prong of the conventional two prong cannula. For example, a conventional two prong cannula has a total volumetric flowrate $Q_2$ and a velocity v, and each prong has a cross-sectional area A. The total volumetric flowrate $Q_2$ is equal to v multiplied by the sum of the prong cross-sectional areas, namely 2A (i.e., $Q_2=2*A*v$). The single prong of the present cannula may have the same cross-sectional area A and outputs breathing gas at the same velocity v, so the volumetric flowrate $Q_1$ of this single prong cannula equals v multiplied by A (i.e., $Q_1=A*v$), which is equal to half of the total volumetric flowrate $Q_2$ of the conventional two prong cannula.

In some implementations, the method further includes receiving, at a second inlet end of the lumen of the cannula body opposite the first inlet end, a second flow of breathing gas, the lumen of the cannula body being continuous between the first inlet end and the second inlet end; and wherein the volume flow rate through the nasal prong from the combined first and second flows of breathing gas is about half the volume flow rate through the one pong of a conventional two prong cannula such that the combined first and second flows of breathing gas is delivered to the patient at a velocity that is about the same as the velocity at which breathing gas is delivered to the patient via the one prong of the conventional two prong cannula. Receiving, at first and second inlet ends of the lumen of the cannula body may further comprise receiving a first flow of breathing gas at a first gas flow rate of 10 liters per minute (L/min) at the first inlet end and receiving a second flow of breathing gas at the second inlet end at a second gas flow rate of 10 L/min. Delivering the first and second flows of breathing gases through the nasal prong may further comprise delivering the first and second flows of breathing gases to the nare at a flow rate of 20 liters per minute (L/min), and wherein the conventional two prong cannula delivers breathing gas to nares at a flow rate of 40 L/min. The method may further include any of altering a cross-sectional shape of the distal end of the nasal prong to maintain a target flow velocity; heating the first flow; and humidifying the first flow and the second flow.

In an aspect, a cannula for providing respiratory therapy to a patient may include a cannula body having a lumen extending continuously from a first inlet end to a second inlet end of the cannula body, and a first nasal prong having a proximal end attached to a cannula body and a distal end sized to be inserted into a nare of the patient. The first nasal prong defines a lumen for a flow of breathing gas from a source of breathing gas to the nare of the patient, and the lumen of the first nasal prong extends from the lumen of the cannula body to the distal end of the first nasal prong. The cannula receives a first flow of breathing gas at the first inlet end of the lumen of the cannula body, and receives a second flow of breathing gas at the second inlet end of the lumen of the cannula body. The cannula also delivers the first and second flows of breathing gas to the nare of the patient at a volumetric flow rate through the first nasal prong. The volume flow rate through the first nasal prong from the combined first and second flows of breathing gas is about half a volume flow rate through both prongs of a conventional two prong cannula, such that the combined first and second flows of breathing gas is delivered to the patient at a velocity that is the about the same as the velocity at which breathing gas is delivered to the patient via the one prong of the conventional two prong cannula. For example, a conventional two prong cannula has a total volumetric flowrate $Q_2$ and a velocity v, and each prong has a cross-sectional area A. The total volumetric flowrate $Q_2$ is equal to v multiplied by the sum of the prong cross-sectional areas, namely 2A (i.e., $Q_2=2*A*v$). The single prong of the present cannula may have the same cross-sectional area A and outputs breathing gas at the same velocity v, so the volumetric flowrate $Q_1$ of this single prong cannula equals v multiplied by A (i.e., $Q_1=A*v$), which is equal to half of the total volumetric flowrate $Q_2$ of the conventional two prong cannula.

Numerous examples are available for adapting and implementing the assemblies and methods described herein. For example, the cannulas and nasal prongs described herein may be used with respiratory therapy devices including mechanical ventilation, oxygen masks, Venturi masks, tracheotomy masks, Assist/Control Ventilation, Intermittent Mandatory Ventilation, Pressure Support Ventilation, Continuous Positive Airway Pressure (CPAP) treatment, Bi-Level Positive Airway Pressure (BiPAP), Non-invasive Ventilation (NIV), Non-Invasive Positive Pressure Ventilation (NIPPV), and Variable Positive Airway Pressure (VPAP). The therapy is used for treatment of various respiratory conditions including Sleep Disordered Breathing (SDB) and Obstructive Sleep Apnea (OSA).

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 4A shows a simulation of $CO_2$ concentration in an airway provided with breathing gas at a flow rate of 20 L/min through a single prong cannula;

FIG. 4B shows a simulation of a $CO_2$ concentration in an airway provided with breathing gas at a flow rate of 40 L/min through a dual prong cannula;

FIG. 5 shows a circular nasal prong;

DETAILED DESCRIPTION

To provide an overall understanding of the assemblies and methods described herein, certain illustrative implementations will be described. Although the implementations and features described herein are specifically described for a nasal cannula for providing respiratory therapy to a patient, it will be understood that all the components and other features outlined below may be combined with one another in any suitable manner and may be adapted and applied to respiratory therapy devices, including low flow oxygen therapy, continuous positive airway pressure therapy (CPAP), bi-level positive airway pressure therapy (BiPAP), mechanical ventilation, oxygen masks, Venturi masks, and Tracheostomy masks.

As used herein, the term "about" should be understood to mean within plus or minus 20% of a value. For example, "about 40 cm" should be understood to mean the range of 32 cm to 48 cm.

Figure 1:
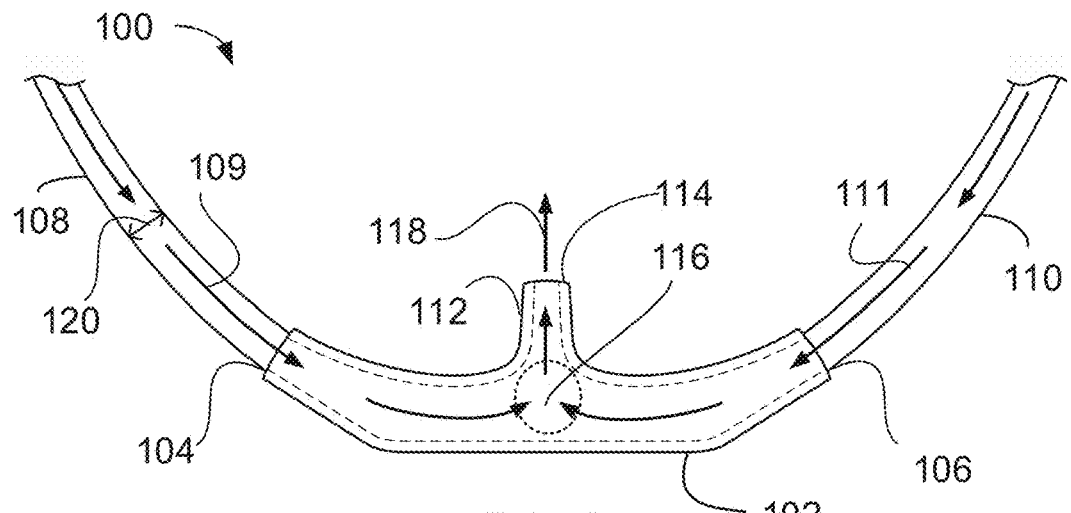
FIG. 1 shows a single prong nasal cannula providing two flows of breathing gas through a single prong.

FIG. 1 shows a single prong nasal cannula 100 providing two flows of breathing gas to a patient through the single prong. The single prong nasal cannula 100 includes a cannula body 102 having a first inlet end 104 and a second inlet end 106. The cannula body 102 forms an internal lumen between the first inlet end 104 and the second inlet end 106. A first flow of breathing gas 109 is provided to the first inlet end 104 through a first gas tube 108, and a second flow of breathing gas 111 is provided to the second inlet end 106 through a second gas tube 110. The first flow of breathing gas 109 and the second flow of breathing gas 111 meet in a center of the cannula body 102 forming a turbulent region 116.

The first flow of breathing gas 109 and the second flow of breathing gas 111 exit the cannula body 102 through a distal end 114 of a nasal prong 112 in a flow of breathing gas 118 to the patient's nare.

A single prong nasal cannula 100 having a single nasal prong 112 as shown in FIG. 1 can provide the same effective flush as a conventional dual prong cannula when the single nasal prong 112 is sized to maintain the same flow velocity, even when the volume flow rate of the breathing gas through the single prong nasal cannula 100 is half that of the dual prong cannula. For example, a conventional dual prong cannula has a total volumetric flowrate $Q_2$ and a velocity v, and each prong has a cross-sectional area A. The total volumetric flowrate $Q_2$ is equal to v multiplied by the sum of the prong cross-sectional areas, namely 2A (i.e., $Q_2=2*A*v$). Single prong 112 of cannula 100 may have the same cross-sectional area A and outputs breathing gas at the same velocity v, so the volumetric flowrate $Q_1$ of cannula 100 equals v multiplied by A (i.e., $Q_1=A*v$), which is equal to half of the total volumetric flowrate $Q_2$ of the conventional dual prong cannula.

As shown in FIGS. 4A and 4B, the flush of a patient's airways provided by a single prong cannula with a flow rate of 20 liters per minute (L/min) to a patient having a closed mouth (FIG. 4A) is equivalent to or greater than the flush of the patient's airways provided by a conventional dual prong cannula with a flow rate of 40 L/min to a patient having a closed mouth (FIG. 4B). FIGS. 4A and 4B illustrate a comparative study of effective flush of the anatomic airways by computational fluid dynamics (CFD) based on a simulated female airway based on MRI data. The model of the airway includes the upper airway and part of the trachea of a patient. The cannulas were simulated from a CAD model of the cannula tips for comparison, and the condition at the tip of the cannula was defined by a flow of 50% O2 and 75% relative humidity, with a constant flow rate maintained throughout the simulation. The model simulates a patient's breathing supported by a single prong cannula (FIG. 4A) and a conventional dual prong cannula (FIG. 4B). FIGS. 4A and 4B illustrate the concentration of $CO_2$ in the airway just before inhalation, and the shading of the airway indicates the expected $CO_2$ concentration in the airway with darker regions indicating higher $CO_2$ concentration.

FIG. 4A shows a simulation 400 of the flush of the patient's upper airway 402a and trachea 404a provided by a single prong cannula with a flow rate of 20 L/min provided to the patient's nare 406a when the patient's mouth 408a is closed. As illustrated in FIG. 4A, the upper airways and upper portion of the trachea are largely free of $CO_2$.

FIG. 4B shows a simulation 401 of the flush of the patient's upper airway 402b and trachea 404b provided by a dual prong cannula with a flow rate of 40 L/min provided to the patient's nare 406b when the patient's mouth 408b is closed. Compared to FIG. 4B, FIG. 4A shows a different distribution of $CO_2$, but the total mass of $CO_2$ is nearly identical to that shown in FIG. 4B. By maintaining a high velocity of flow through the single prong, the flush of $CO_2$ from the patient's airway is equivalent despite only providing gas flow through a single prong, at half the flow rate as provided by a conventional dual prong cannula.

The single prong nasal cannula 100 may provide the benefits of increased patient comfort and increased flush relative to the gas flow rate, even when the single prong nasal cannula 100 includes a second prong not designed to provide a flow of gas to the patient's nare (a "dummy" prong). A second nasal prong may aid in stabilizing the cannula on the patient's face, while not interfering with flush through the patient's second nare. The single prong cannula 100 may further include ports for administration of medicament or additional streams of breathing gas. Further, the single prong cannula 100 may provide breathing gas to the patient which is one or more of heated, humidified, and medicated.

Alternative designs of single prong cannulas may include different configurations of the cannula body. For example, FIGS. 2 and 3 show single prong nasal cannulas having alternative cannula body configurations to provide a breathing gas to a patient's nare.

Figure 2:
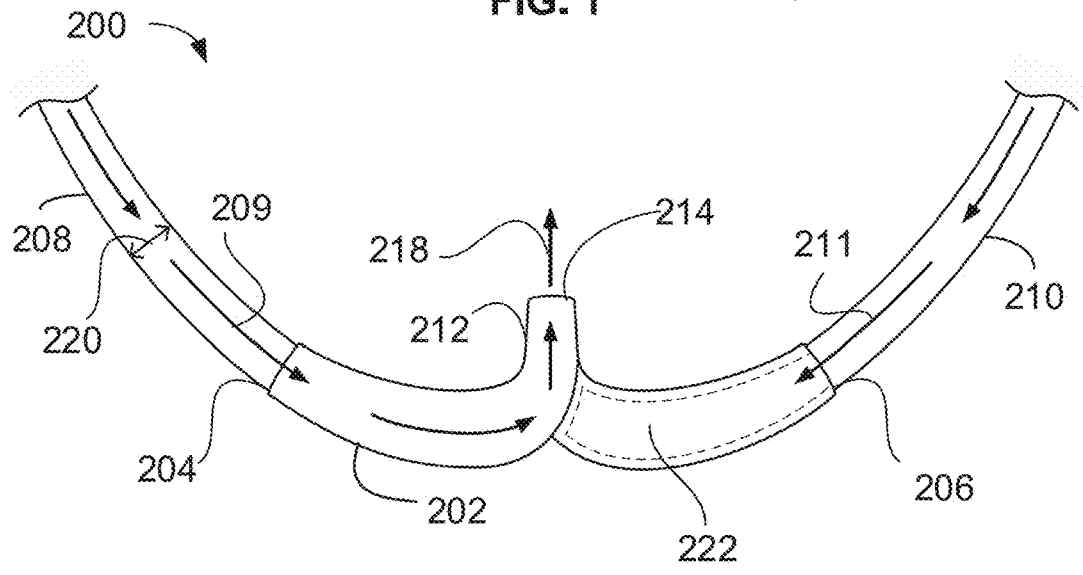
FIG. 2 shows a single prong nasal cannula providing one flow of breathing gas through a single prong.

FIG. 2 shows a single prong nasal cannula 200 providing one flow of breathing gas through a single nasal prong 212. The nasal cannula 200 includes a cannula body 202 including a first inlet end 204 and a second end 206. The cannula body 202 further includes a nasal prong 212 having a distal end 214 for insertion into a patient's nare. The cannula body 202 forms a lumen from the first inlet end 204 to the distal end 214 of the nasal prong 212. A first flow of breathing gas 209 is provided to the first inlet end 204 through a first tube 208, and the first flow of breathing gas 209 is then provided through the nasal prong 212 where it exits as a flow of breathing gas into the patient's nares 218.

The second end 206 of the cannula body 202 is not fluidically coupled to the first inlet end 204 or the nasal prong 212. Instead, the cannula body 202 may include a closed portion 222 coupled to a second tube 210. The second tube 210 may include a second flow of breathing gas 211 flowing through. However, the second flow of breathing gas 211 through the second tube 210 is not necessary as the second flow of breathing gas 211 is not provided to the patient. The second tube 210 aids in stabilizing the cannula body 200 on the patient's face. By providing the single first flow of breathing gas 209 to the patient through the nasal prong 214, there is no region of turbulence where two breathing gas flows meet in the cannula body, such as described above in regard to nasal cannula 100 of FIG. 1.

Figure 3:
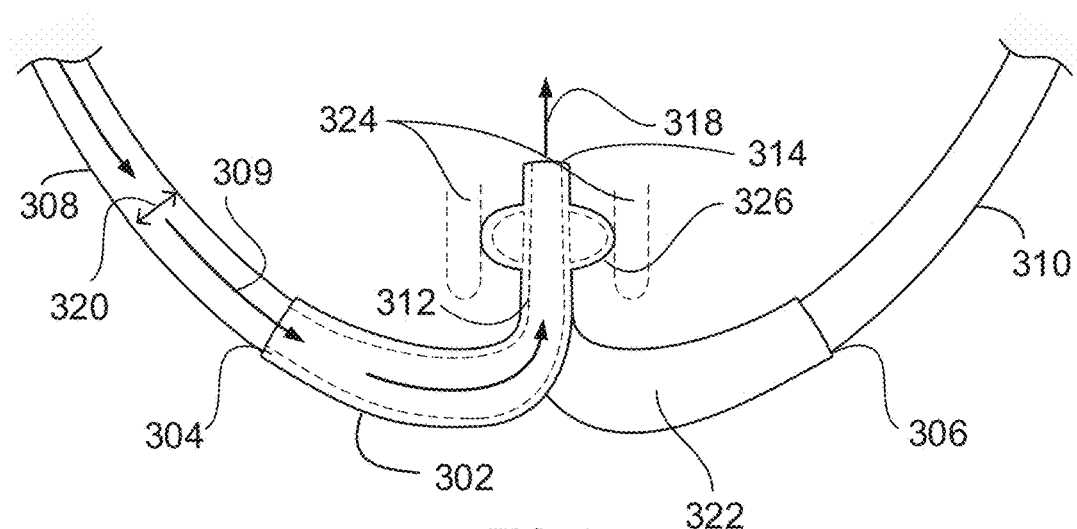
FIG. 3 shows a single prong nasal cannula including a nasal pillow providing one flow of breathing gas to a patient's nare.

FIG. 3 shows a single prong nasal cannula 300, such as the nasal cannula 200 of FIG. 2, including a nasal pillow 326. The nasal cannula 300 includes a cannula body 302 including a first inlet end 304 and a second end 306. The cannula body 302 further includes a nasal prong 312 having a distal end 314 for insertion into a patient's nare. The cannula body 302 forms a lumen from the first inlet end 304 to the distal end 314 of the nasal prong 312. A first flow of breathing gas 309 is provided to the first inlet end 304 through a first tube 308, and the first flow of breathing gas 309 is then provided through the nasal prong 312 where it exits as a flow of breathing gas into the patient's nare 318.

The second end 306 of the cannula body 302 is not fluidically coupled to the first inlet end 304 or the nasal prong 312, and, as described above with regard to the nasal cannula 200 of FIG. 2, no flow of breathing gas need be provided through the second gas tube 310 to the second end 306 of the cannula body 302.

The nasal prong 312 includes a nasal pillow 326 sized to fit within the nare 324 of a patient. The nasal pillows 326 extend orthogonally from the external surface of the nasal prong 312. The nasal pillows 326 may extend fully around the outer circumference of the nasal prong 312 so as to circumscribe the nasal prong 312. The nasal pillow 326 may be formed from a deformable material so as to be adaptable to different sized or shaped nares, and may be formed as a dome shape or other shape configured to comfortably fit within the nare 324. The nasal pillow 326 may be sized to extend from the external surface of the nasal prong 312 to an internal surface of the patient's nare 324 so as to occlude the patient's nare into which the flow of breathing gas 318 is provided. By occluding the nare 324 into which the flow of breathing gas 318 is provided, no breathing gas escapes the nare 324 (via the space between the nare 324 and the nasal prong 312). If the breathing gas includes medicament, the medicament is then provided to the patient in a known quantity and dosage. Further, occlusion of the nare 324 decreases entrainment of air near the nare 324 into the flow of breathing gas 318.

As described above with regard to cannula 100 in FIG. 1, a second nasal prong may be provided for stability of the cannula body, though the second nasal prong is not designed to provide a flow of breathing gas to the patient's second nare. The second nasal prong may or may not have a lumen. The second nasal prong, when provided on the cannula body 300, may not include a nasal pillow such as nasal pillow 326, so that $CO_2$ can be expelled through the patient's second nare to improve effective flush of the patient's airways.

In order to provide an effective flush of the patient's airways through a single nasal prong cannula, such as nasal cannulas 100, 200 and 300 of FIGS. 1-3, a variable geometry nasal prong may be provided such that the velocity of the breathing gas provided to the patient's nare is maintained despite a reduced breathing gas flow rate through the nasal cannula. A variable geometry nasal prong provides an improvement over the conventional circular nasal prong 500 described below in FIG. 5.

FIG. 5 shows a conventional circular nasal prong 500. Conventionally, nasal prongs are circular in shape and are sized to fit within a patient's nares. The nasal prong 512 includes a circular distal end 514 forming a circular lumen 528. The nasal prong 512 has a diameter 530 of the circular lumen 528.

A flow of breathing gas provided to the nasal prong 512 will result in a flow of breathing gas expelled from the distal end 514 of the nasal prong 512 having a particular velocity. The velocity of the flow provided by the nasal prong 512 is determined both by the flow rate of the provided breathing gas and the cross-sectional area of the lumen through which the gas flows.

For example, a nasal prong 512 having a diameter 530 of 3 mm has a circular lumen 528 with a cross-sectional area of about 7 $mm^2$. When a breathing gas is provided at a high flow rate of 20 L/min, the velocity of the flow provided to the patient's nare is 48 m/s. When a breathing gas is provided at a medium flow rate of 10 L/min, the velocity of the flow provided to the patient's nare from the circular lumen 528 is 24 m/s. When a breathing gas is provided at a low flow rate of 5 L/min, the velocity of the flow provided to the patient's nare from the circular lumen 528 is 12 m/s. Lowering the flow rate of gas provided to the nasal prong 512 results in a reduction of flow velocity provided to the patient's nares through the lumen 528.

In some situations, a reduced flow rate of breathing gas is preferred to improve patient comfort. A lower flow rate can be accomplished with gas sources that have a limited maximum output, such as a portable oxygen canister or oxygen concentrator combined with a blower in a home-based treatment device, and a lower flow rate may also have a lower associated amount of noise. In order to overcome the lowered flow velocity that occurs with lowered flow rate, the geometry of the nasal prong can be changed. Conventionally, the cannula may be changed for another differently sized cannula to provide a nasal prong with a smaller cross-sectional area; however changing the cannula may be confusing or difficult for a patient.

A method for changing the cross-sectional area of the lumen without actually changing the cannula is to provide a nasal prong with a variable geometry. The single prong may be manufactured to allow the prong to assume multiple geometries depending on the flow rate of the breathing gas through the prong. For example, the single prong may be manufactured from a shape memory material, and may change in geometry in response to exposure to an external stimuli. In another example, the single prong may be manufactured from a piezoelectric material and may change in geometry in response to application of an electrical signal. In some implementations, the manufacturing of the single prong results in a shape which is able to passively vary in geometry depending on the flow rate of gas through the prong. Manufacturing techniques to produce nasal prongs having variable geometries are described in greater detail below.

Having a deformable geometry at the interface of the flow opening at the distal end of the nasal prong where the breathing gas exits the cannula into a patient's nare enables the geometry of the nasal prong to change in response to changes in the breathing gas flow rate. By changing the geometry of the nasal prong as the volume flow rate changes, the velocity is maximized at any flow rate without the need to switch cannulas or change the cannula geometry.

Possible variable geometries of the single nasal prong are illustrated in FIGS. 6-13 and are described below. At higher gas flow rates, the high pressure causes the tip of the nasal prong to deform so as to provide a wider opening through which breathing gas may enter the patient's nares. At lower flow rates, the lower pressure allows the opening at the tip of the nasal prong to close up to form an opening with a smaller cross-section which minimizes reduction in flow velocity of the breathing gas leaving the cannula.

While having a variable geometry enables a cannula having a single prong to provide a patient with a flow velocity at lower flow rates that is equivalent or nearly equivalent to the flow velocity at high flow rates, conventional dual prong cannulas may also benefit from having prongs of variable geometry. Prongs of variable geometry generally allow for control of flow velocity regardless of variations in the gas flow rate provided to the prongs. The variable geometry prong designs illustrated in FIGS. 6-13 and described below are applicable to any of the single prong cannulas illustrated in FIGS. 1-3 and described above, or to dual prong cannulas.

Figure 6A:
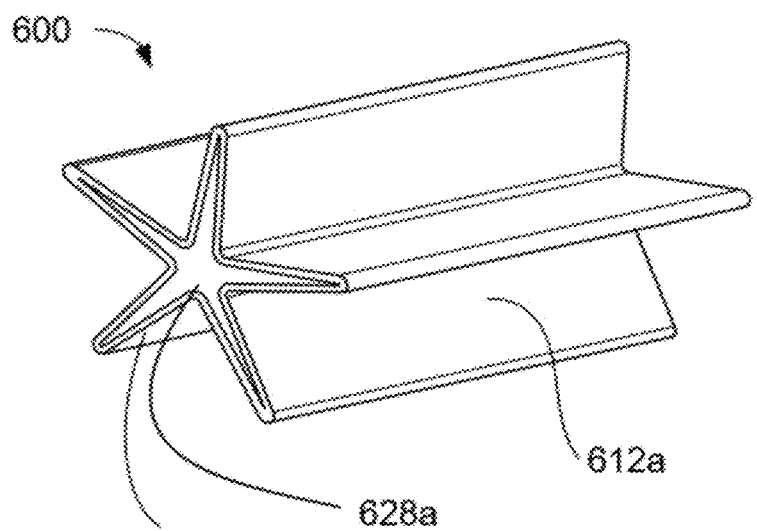
FIG. 6A shows a five-pointed star shape of a geometrically variable nasal prong at a low gas flow rate.
Figure 6B:
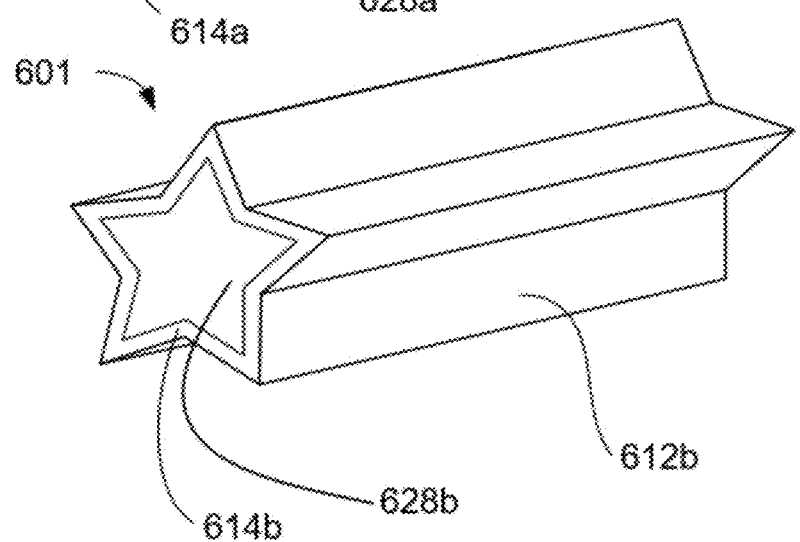
FIG. 6B shows a shape of a geometrically variable nasal prong at a medium gas flow rate.
Figure 6C:
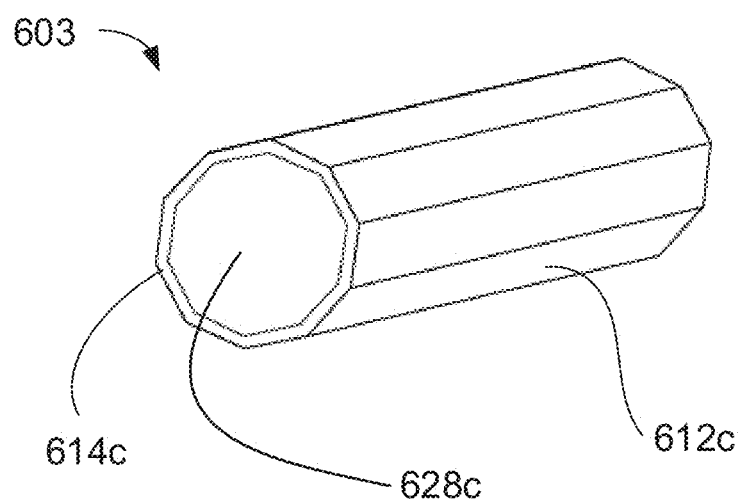
FIG. 6C shows a shape of a geometrically variable nasal prong at a high gas flow rate.

FIGS. 6A-C illustrate a variable geometry cannula and the deformation of the cannula at various gas flow rates. The variable geometry of the distal end of the nasal prong enables the lumen to bend, fold, or collapse to provide a smaller cross-sectional area for breathing gas to flow through when breathing gas is provided at low flow rates, while at higher flow rates the breathing gas expands the distal end of the nasal prong to a larger cross-sectional area. With a distal end geometry that varies with the flow rate of the breathing gas, the breathing gas can be provided to the patient at a constant velocity or a minimally reduced velocity despite variations in the flow rate of the provided gas. The velocity of the breathing gas exiting a distal end of the nasal prong in any of FIGS. 6A-C would be equal to or higher than the velocity of breathing gas supplied by the conventional circular nasal prong as illustrated in FIG. 5.

FIG. 6A shows a five-pointed star shape of a geometrically variable nasal prong 600 at a low gas flow rate. The nasal prong 600 includes an external prong wall 612a at a distal end 614a of the nasal prong 600. The shape of the distal end 614a of the nasal prong 600 is folded to form a five-pointed star, such that a small cross-sectional area of the lumen 628a is provided at the distal end 614a for breathing gas to flow through. The small cross-sectional area of the lumen 628a provides the breathing gas to the nare at an increased velocity even when a flow rate of the gas is low. For example, at a low flow rate of 5 L/min, the cross-sectional area of the lumen 628a may be about 3.5 mm$^2$, and the velocity of the flow of breathing gas through the lumen 628a may be about 24 m/s. This velocity is double the velocity of the breathing gas through the conventional circular prong described in FIG. 5 at the same low flow rate.

The cross-sectional area of the lumen 628a at the distal end 614a of the nasal prong 600 is dependent on the flow rate of the breathing gas provided through the nasal prong 600. The variable shape of the distal end 614a of the nasal prong 600 may take on other shapes as the gas flow rate through the nasal prong 600 is changed, as described below with respect to FIGS. 6B and 6C.

FIG. 6B shows a shape of a geometrically variable nasal prong 601 at a medium gas flow rate. The nasal prong 601 includes an external prong wall 612b at a distal end 614b of the nasal prong 601. The shape of the distal end 614b of the nasal prong 601 is folded to form a five-pointed star having a larger cross-sectional area of the lumen 628b than the cross-sectional area of the lumen 628a of nasal prong 600 in FIG. 6A. The distal end 614b of the nasal prong 601 assumes this shape when the flow rate of the breathing gas provided to the nasal prong 601 is higher. The higher flow rate of the breathing gas expands the distal end 614b of the nasal prong 601 to provide the gas to a patient at a similar velocity as provided through the lumen 628a of nasal prong 600 in FIG. 6A. For example, at a medium flow rate of about 10 L/min, the cross-sectional area of the lumen 628b may be about 5 mm$^2$, and the velocity of the flow of breathing gas through the lumen 628b may be about 33 m/s. This velocity is higher than the velocity of the breathing gas through the conventional circular prong described in FIG. 5 at the same medium flow rate.

FIG. 6C shows a shape of a geometrically variable nasal prong 603 at a high gas flow rate. The nasal prong 603 includes an external prong wall 612c at a distal end 614c of the nasal prong 603. The shape of the distal end 614c of the nasal prong 603 is expanded to a dodecagon with a nearly circular cross-sectional shape. The nasal prong 603 assumes the expanded geometry when breathing gas is provided at a high flow rate. The expanded geometry of the distal end 614c enables breathing gas to flow through the lumen 628c of the nasal prong 603 into the patient's nare with a velocity similar to the velocity of the breathing gas provided by the folded shapes of nasal prongs 601 and 600 of FIGS. 6A and 6B at lower flow rates of breathing gas. For example, at a high flow rate of 20 L/min, the cross-sectional area of the lumen 628c may be about 7 mm$^2$, and the velocity of the flow of breathing gas through the lumen 628c may be about 48 m/s. This velocity is equal to the velocity of the breathing gas through the conventional circular prong described in FIG. 5 at the same high flow rate. Accordingly, the velocity of the breathing gas provided to the patient at high flow rates is maintained with the variable geometry prongs, the reduction in velocity at lower flow rates is minimized with the variation of the geometry to decrease the cross-sectional area through which the gas flows to the patient. This allows for little to no variation in flush of the patient's upper airway and trachea.

The variable geometry of nasal prongs 600, 601 and 603 of FIGS. 6A-6C allows the breathing gas to be provided to the patient at a lower flow rate than typically used, while still providing the gas to the patient's nares with a sufficient velocity to flush the patient's airways. The lower flow rate of gas may be required in situations where no wall-source of breathing gas is available, such as in home care settings. Further the lower flow rate of gas may be more comfortable for the patient.

While the nasal prongs 600, 601 and 603 of FIGS. 6A-C show geometries based on a ten-sided polygon, nearly any geometric shape may be employed in forming a variably shaped nasal prong. In some embodiments, the distal end of the nasal prong is formed as a regularly-sided polygon, a circle, an ellipse, or a non-regularly sided polygon. The distal end of the nasal prong can be formed with either an odd or an even number of sides. The geometric shape of the distal end need only be formed such that a smaller cross-sectional area of the distal lumen can be formed at lower flow rates to increase the velocity of the breathing gas as it flow through the smaller lumen. Further examples of cross-sectional shapes which can allow a nasal prong to provide a constant velocity breathing gas to a patient are illustrated in FIGS. 7-13.

Figure 7:
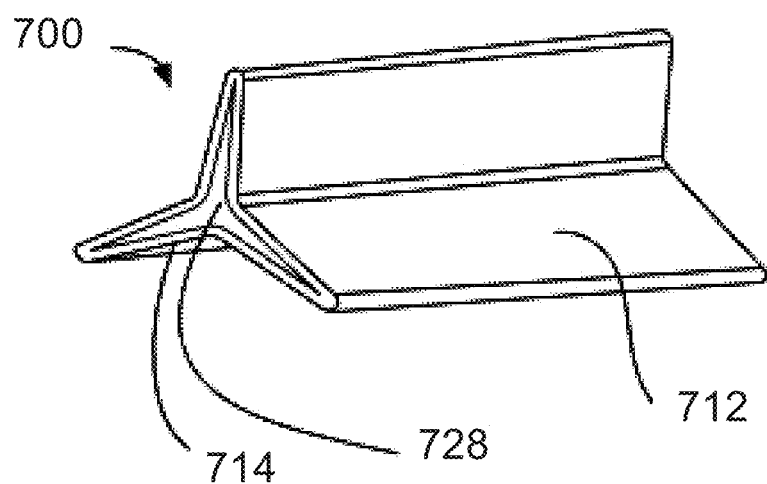
FIG. 7 shows a three-pointed star shape of a geometrically variable nasal prong.

The distal end of the nasal cannula can be formed in multiple star-shapes having any number of lobes or points. While FIGS. 6A and 6B show a five-pointed star shape, FIG. 7 shows a three-pointed star shape of a geometrically variable nasal prong 700. The nasal prong 700 has an external surface 712 which is variable at a distal end 714 from the three-pointed star shape at low flow rates to a hexagonal shape at high flow rates. The cross-sectional area of the lumen 728 through which the breathing gas can flow through is variable by the changing shape of the external surface 712. As described above, at low flow rates the nasal prong 700 assumes the folded shape having a smaller cross-sectional area, while at higher flow rates, the flow of gas expands the nasal prong 700 distal end 714 to a larger cross-sectional area through which the breathing gas can flow.

FIGS. 6 and 7 show nasal prongs having geometrically variable shapes which may be formed by injection molding.

Figure 8:
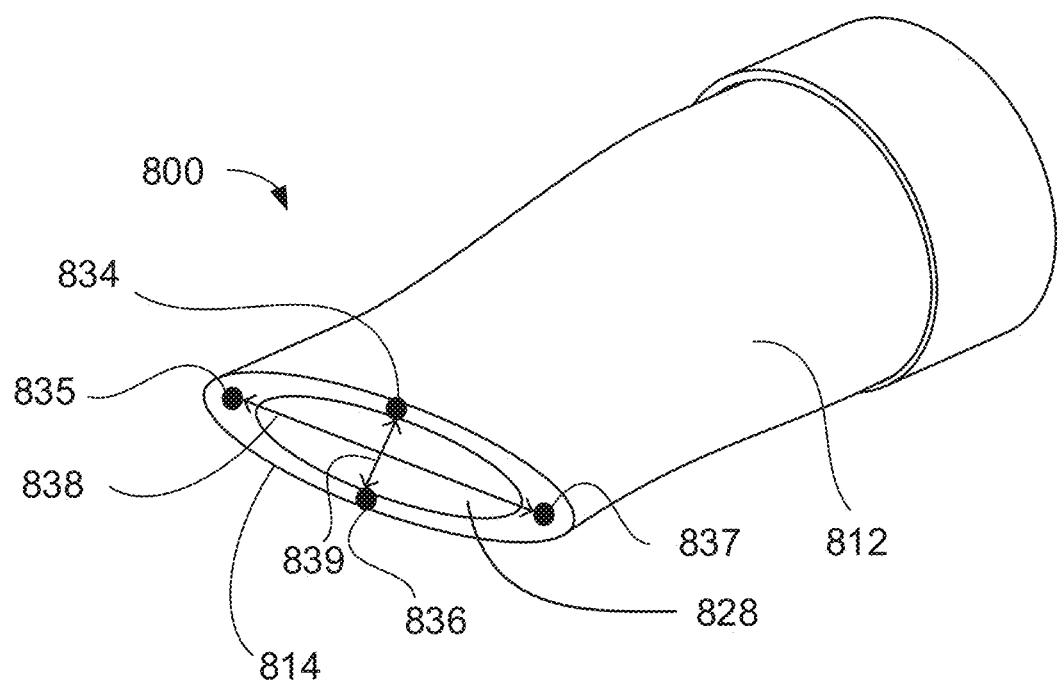
FIG. 8 shows an elliptical shape of a geometrically variable nasal prong.

FIG. 8 shows an oval or elliptical shape of a geometrically variable nasal prong 800. The nasal prong 800 includes a distal end 814, and an external surface 812 which defines a lumen 828 through which the breathing gas flow to the patient's nare. The distal end 814 is variable in geometry from a circular shape to an elliptical shape depending on the rate of flow of the breathing gas provided through the nasal prong 800. The shape of the distal end 814 can be described based on the distance between four points on the distal end 814 of the nasal prong 800. A first distance 838 extends between a first point 834 and a second point 836 opposite the first point 834, and a second distance 839 extends between a third point 835 and a fourth point 837 positioned opposite the third point 835, where the third point 835 is equidistant from both the first point 834 and the second point 836. At a higher flow rate of breathing gas flow through the nasal prong 800, the difference between the first distance 838 and the second distance 839 is less than the difference between the first distance 838 and the second distance 839 at a low flow rate of breathing gas. Accordingly, at a high rate of flow, the distal end 814 of the nasal prong 800 assumes a more circular shape which is more open. At a lower rate of flow, the distal end 814 of the nasal prong 800 takes on an elliptical or oval shape. At a low flow rate of breathing gas through the nasal prong 800, the distal end 814 may also include flattened ends at the second point 835 and fourth point 837 to further reduce the cross-sectional area of the lumen 828.

Figure 9:
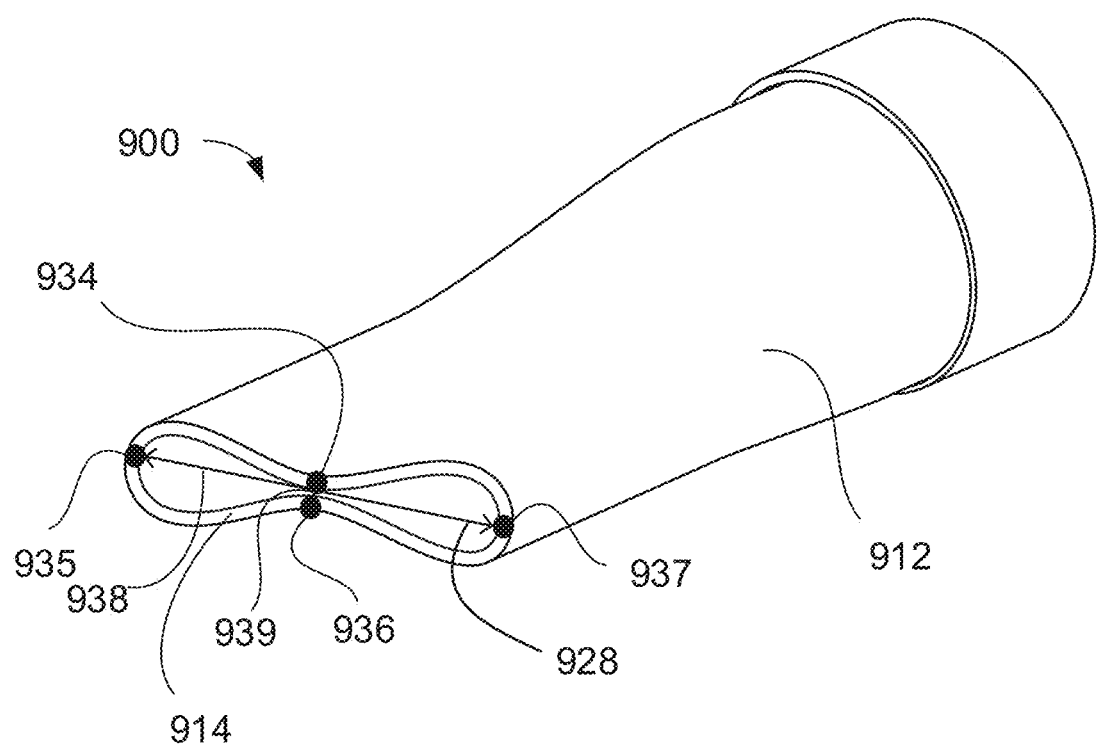
FIG. 9 shows a pinched elliptical shape of a geometrically variable nasal prong.

FIG. 9 shows a pinched elliptical or oval shape of a geometrically variable nasal prong 900. The nasal prong 900 includes a distal end 914, and an external surface 912 which defines a lumen 928 through which the breathing gas flow to the patient's nare. The distal end 914 is variable in geometry from a circular shape to a pinched elliptical shape depending on the rate of flow of the breathing gas provided through the nasal prong 900. The distal end 914 may also pass through a geometry similar to the elliptical shape of nasal prong 800 in FIG. 8.

Like the nasal prong 800 described in FIG. 8, the shape of the distal end 914 can be described based on the distance between four points on the distal end 914 of the nasal prong 900. A first distance 938 extends between first point 934 and a second point 936 opposite the first point 934, and a second distance 939 extends between a third point 935 and a fourth point 937 positioned opposite the third point 935 on the distal end 914 of the nasal prong 900, where the third point 935 is equidistant between the first point 934 and the second point 936. At a higher flow rate of breathing gas flow through the nasal prong 900, when the distal end 914 of the nasal prong 900 is in the expanded state, the difference between the first distance 938 and the second distance 939 is less than the difference between the first distance 938 and the second distance 939 at a low flow rate of breathing gas. When a low flow rate of breathing gas is provided through the nasal prong 900, the first point 934 and the second point 936 become closer to each other than the third point 935 is to the fourth point 937, such that the first distance 938 becomes larger than the second distance 939. In this state, two sides of the distal end 914 of the nasal cannula 900 become pinched toward each other, and the pinched cannula has a hippopede shape, like a figure-eight or an infinity symbol. The distal end 914 may have flattened or concave sides depending on the flow rate of the provided breathing gas. At high flow rates, the distal end 914 of the nasal cannula 900 may expand again toward a circular shape, and the distal end 914 can assume any geometry between the pinched-oval and fully circular shape depending on the flow rate of the gas flowing through the nasal prong 900.

FIGS. 8 and 9 show nasal prongs having geometrically variable shapes which may be formed by dip molding, as described below with regard to FIG. 16.

Figure 10:
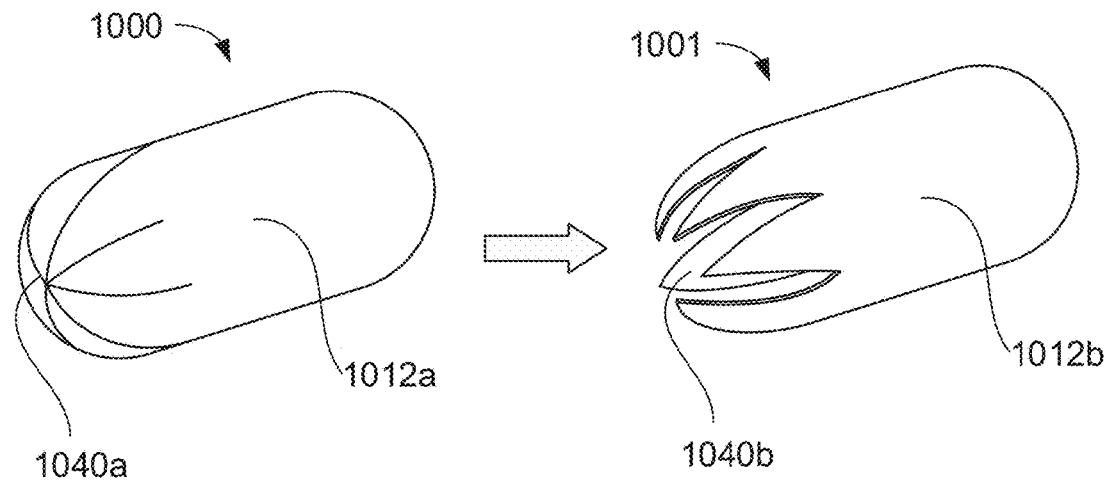
FIG. 10 shows a geometrically variable nasal prong in a closed and open configuration.

FIG. 10 shows a geometrically variable nasal prong in a closed configuration 1000 slits may be formed by cutting the dome-shaped tip in a knife edge and open configuration 1001. In the closed configuration 1000, the nasal prong has an external surface 1012a and a dome-shaped distal tip 1040 having slits in a radial pattern. In the closed configuration 1000, the slits are closed at the distal tip 1040. In the open configuration 1001, the nasal prong has an external surface 1012b. The dome-shaped tip of the closed configuration 1000 is instead opened to create an opening 1040b at the distal tip through which breathing gas can flow to the patient. The size of the opening 1040b can vary depending on the flow rate of the supplied breathing gas so that a constant velocity of breathing gas is provided to the patient.

Figure 11:
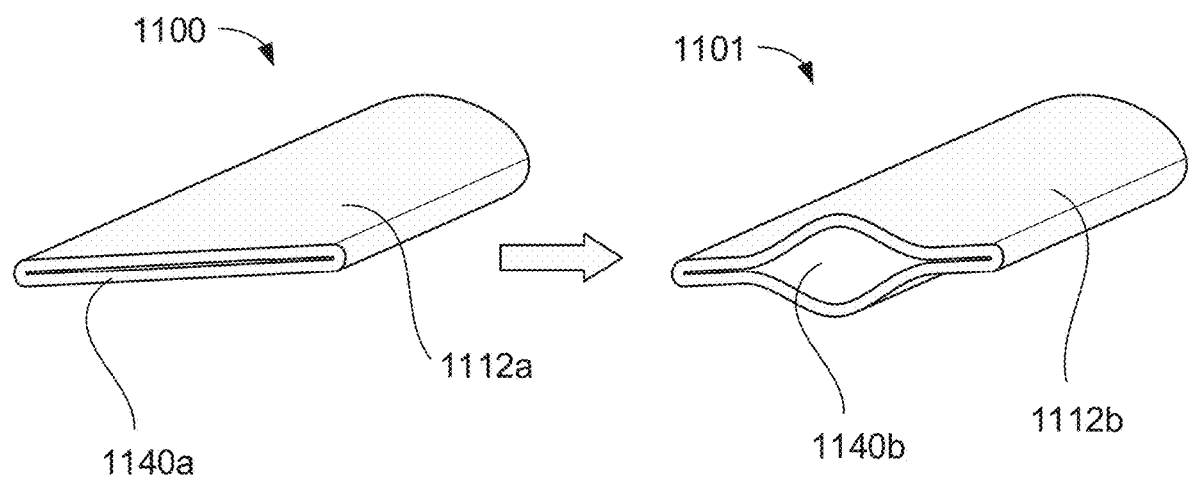
FIG. 11 shows a geometrically variable nasal prong in a closed and open configuration.

FIG. 11 shows a geometrically variable nasal prong in a closed configuration 1100 and open configuration 1101. In the closed configuration 1100, the nasal prong has an external surface 1112a and a distal end 1140a formed as a flat tip where the two sides of the distal opening are touching. In the open configuration 1101, the external surface of the nasal prong 1112b extends to the distal end where a mouth-shaped slot 1140b is formed through which breathing gas can flow to the patient. The distal end 1112b may have a shape like a double-pointed tear drop. There may be little or no flow through the closed-configuration 1100, while in the open configuration 1101 the cross-sectional area defined by the mouth-shaped slot 1140b can be changed based on the provided gas flow rate to provide a nearly constant velocity of breathing gas.

Figure 12:
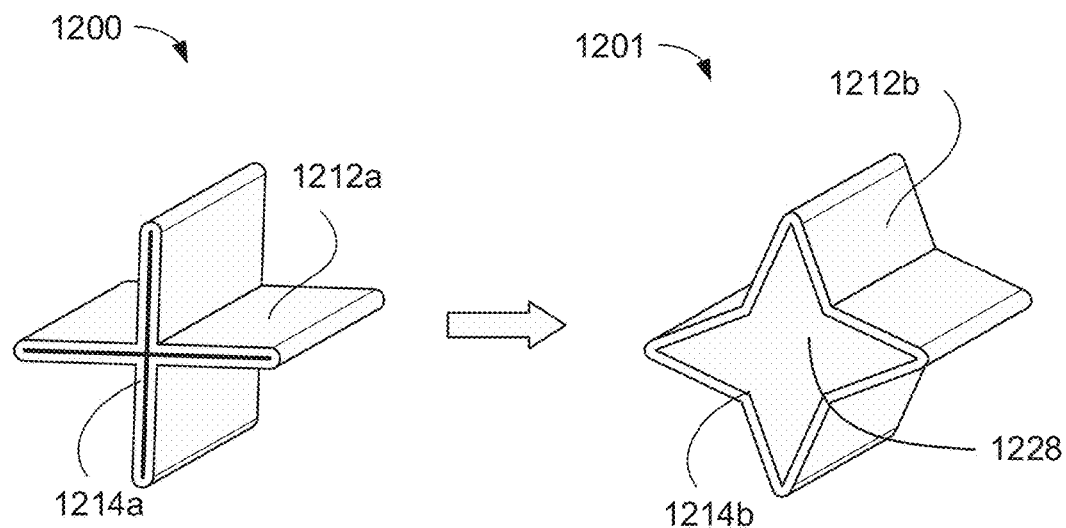
FIG. 12 shows a geometrically variable nasal prong in a closed and open configuration.

FIG. 12 shows a geometrically variable nasal prong in a closed configuration 1200 and open configuration 1201. In the closed configuration 1200, at low flow rates, the external surface of the nasal prong 1212a extends to a distal end 1214a formed as a closed-slotted cross through which little or no flow of breathing gas is provided. In the open configuration 1201, at higher flow rates, the external surface of the nasal prong 1212b is expanded to provide at the distal end 1214b a four-pointed star shaped lumen 1228 through which breathing gas is provided to the patient's nares. Although the lumen in the closed configuration 1200 is closed to form a four-pointed cross, any number of slots may be provided in a shape having any number of lobes or points which remain closed or nearly closed when there is no flow, and is expanded as the flow rate is increased to the open configuration 1201.

Figure 13:
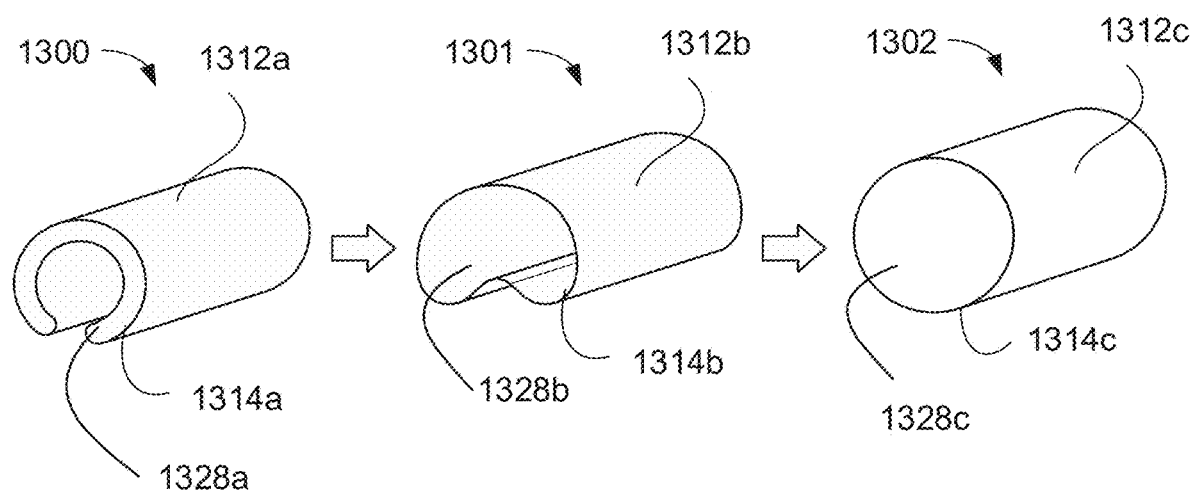
FIG. 13 shows a geometrically variable nasal prong in a closed state, intermediate state, and an open state.

FIG. 13 shows a geometrically variable nasal prong in a closed state 1300, intermediate state 1301, and an open state 1302. In the closed state 1300, the nasal prong 1312a has a distal end 1314a which includes a lumen 1328a shaped as a closed or nearly closed crescent. The nasal prong assumes the closed state 1300 including a crescent-shaped lumen when there is no flow of breathing gas or breathing gas provided at a very low rate. In the intermediate state 1301, the nasal prong 1312b assumes a shape in which a distal end 1314b has a lumen 1328b which is expanded from the closed configuration 1300 to have a kidney-shape through which breathing gas may flow to the patient. In the open state 1302, the nasal prong 1312c has a distal end 1314c which assumes an expanded shape having a circular or nearly circular lumen 1328c. The inner lobe which forms the small concave side of the kidney-shape in the intermediate state 1301 can flip open to provide the circular shape in the open configuration 1302 when higher flow rates of breathing gas are provided. By varying the shape of the lumen depending on the flow rate of the breathing gas, the velocity at which the gas is provided to the patient can be controlled and maintained no matter the flow rate of the breathing gas.

The shapes of the variable geometry lumens in FIGS. 6-13 are not meant to be exhaustive of possible shapes which will maintain flow velocity to the patient depending on the flow rate of the breathing gas, but merely illustrative. Other possible shapes will be apparent to the skilled person based on the description herein. The variable geometry lumens of FIGS. 6-13 can be automatically adaptable to the flow rate of the breathing gas, such that the distal end of the nasal prong assumes a shape which optimizes the velocity of the breathing gas based on the flow rate. The flow of breathing gas provided to the nasal prong can force the distal end into an open geometry at high flow rates, or at lower flow rates, the nasal prong can return to a predetermined shape which decreases the cross-sectional area through which the breathing gas travels and increases the velocity of the gas provided to the patient. The variable geometry lumens of FIGS. 6-13 can also be manually adjustable, such that an adjustable aperture or needle valve allows the geometry of the lumen to be manually adjusted to match a flow rate of breathing gas and to provide an appropriate breathing gas velocity to the patient. Alternatively, the variable geometry lumens of FIGS. 6-13 may be formed from interchangeable nasal prongs or nasal prong tips to provide different sized orifices.

In order to prevent excitement and vibration of the geometrically shaped nasal prongs at specific frequencies, additional alterations and modifications may be made to the nasal prong. For example, features may be added to the prongs to increase the mass of areas which would vibrate at frequencies close to the natural frequency such as ribs to stiffen the vibrating areas. Additionally or alternatively, changes can be made to the angle of the cannula taper where the nasal prong transitions from a circular geometry to the specific geometry, or to the angle where the nasal prong meets the cannula body.

The variable geometry lumens described in FIGS. 6-13 may be applied to any of the cannulas described in FIGS. 1-3, or to conventional dual prong cannulas. The variable geometry nasal prongs provide an improved flush of the patient's airways, with lower flow rate because a higher velocity is maintained through the adjustment of the cross-sectional area of the lumen at the distal end of the nasal prong. Less energy is consumed when a lower flow rate is utilized and less gas is consumed. Thus, a device which is used with the variable geometry nasal cannulas has better battery operation and can be operated at lowered cost compared to conventional systems, because less tank oxygen is used. Finally, lower flow rates result in lower noise as blower requirements are reduced, resulting in increased patient comfort.

The inner walls of the nasal prong lumen may also be altered to include protrusions or other artefacts in order to improve the turbulence of the gas flow provided to the patient's nare. Increased turbulence of the breathing gas further increases the kinetic energy of the gas when it exits the nasal prong, resulting in higher level of flushing of the patient's breathing cavities. Examples of the protrusions are illustrated in FIGS. 14 and 15 and described below.

Figure 14:
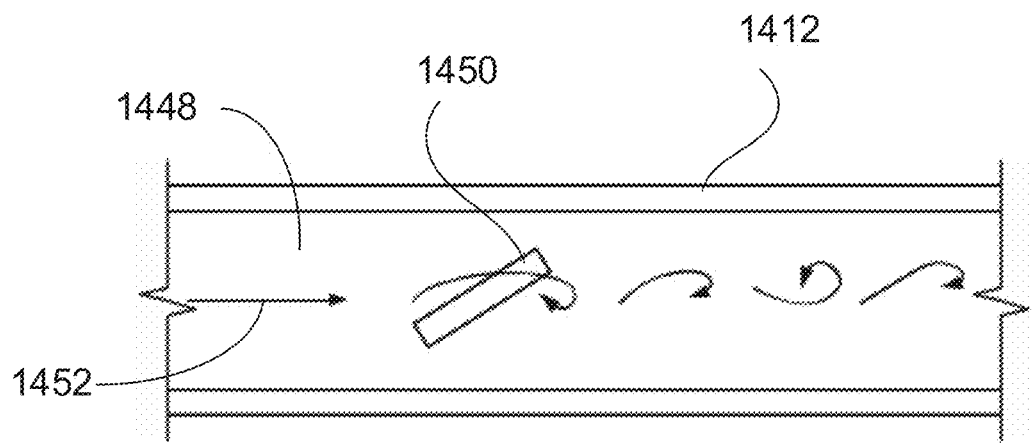
FIG. 14 shows a turbulence-producing protrusion in a nasal prong.
Figure 15:
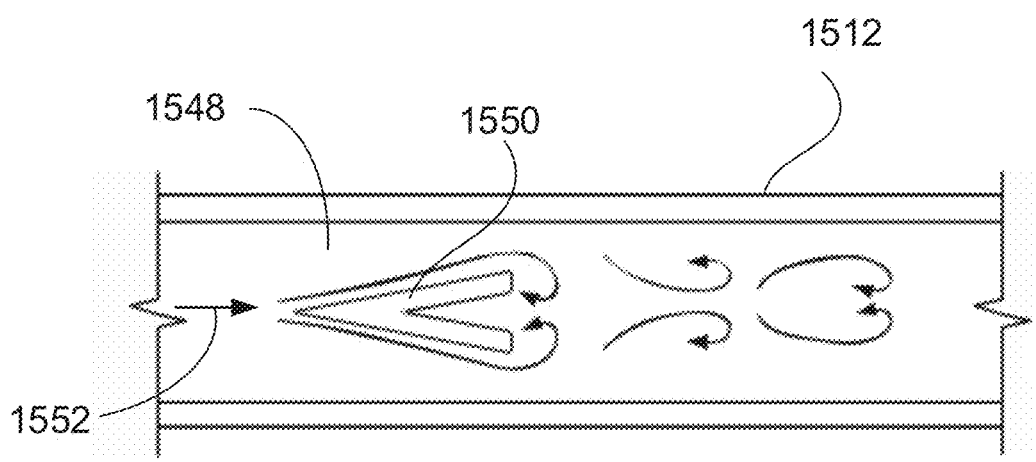
FIG. 15 shows a chevron-shaped turbulence-producing protrusion in a nasal prong.

FIG. 14 shows a turbulence-producing protrusion 1450 in a nasal prong 1412. The nasal prong 1412 has an internal lumen 1448 through which a flow of breathing gas 1452 flows. The internal lumen 1448 includes at least one angled protrusion 1450 which extends into the flow of breathing gas 1452 and produces turbulence in the flow of breathing gas 1452. The increased turbulence increases the kinetic energy of the flow of breathing gas 1452 at the nare and aids in providing effective flush of the patient's airway. The angled protrusion 1450 may be positioned in the internal lumen 1448 at any angle to the flow of breathing gas, for example less than 45° from a longitudinal axis of the nasal prong 1412, at a 45° angle to the longitudinal axis of the nasal prong 1412, or forming more than a 45° angle with the longitudinal axis of the nasal prong 1412.

Turbulence of the flow of breathing gas may be increased by the addition of protrusions of various sizes and shapes. For example, FIG. 15 shows a chevron-shaped turbulence-producing protrusion 1550 in a nasal prong 1512. The nasal prong 1512 has an internal lumen 1548 through which a flow of breathing gas 1552 flows. The internal lumen 1548 includes at least one chevron-shaped protrusion 1550 which extends into the flow of breathing gas 1552 and increases the turbulence of the flow of breathing gas 1552. As shown, the chevron-shaped protrusion has a pointed end and two arms, and may be positioned in the internal lumen 1548 with the pointed end facing into the flow of breathing gas 1552, or may be positioned in any other orientation with respect to the flow of breathing gas 1552.

Protrusions of other shapes that can be added to the inner lumen of the nasal prong to increase turbulence can be envisioned, including raised bumps or lines, triangular protrusions, spiraling protrusions, or protrusions of other shapes or orientations. Similarly, turbulence may be increased by adding indented shapes to the inner walls of the lumen in the flow path of the breathing gas.

Any of the various shapes of the variable geometry nasal prongs of FIGS. 6-13 and the turbulence-producing protrusions of FIGS. 14 and 15 can be manufactured using conventional manufacturing techniques for nasal cannulas including injection molding, liquid silicone molding, or dip molding. In some implementations, the nasal prongs having variable geometry may be produced from a particular material, for example a shape memory material or a piezoelectric material, which enables the geometry of the distal end of the nasal prong to be varied based on the application of a signal or stimulus. The process for producing the nasal cannulas by dip molding is described below in FIG. 16. In a dip-molding process, concave areas of fill up with material creating thick walled sections, while small radius convex areas form thinner walls. In particular, geometrically variable shapes such as the elliptical, pinched oval or pinched elliptical, and radially slotted designs are likely to be dip-molded, though they can be produced by any of the other conventional techniques described above.

Figure 16:
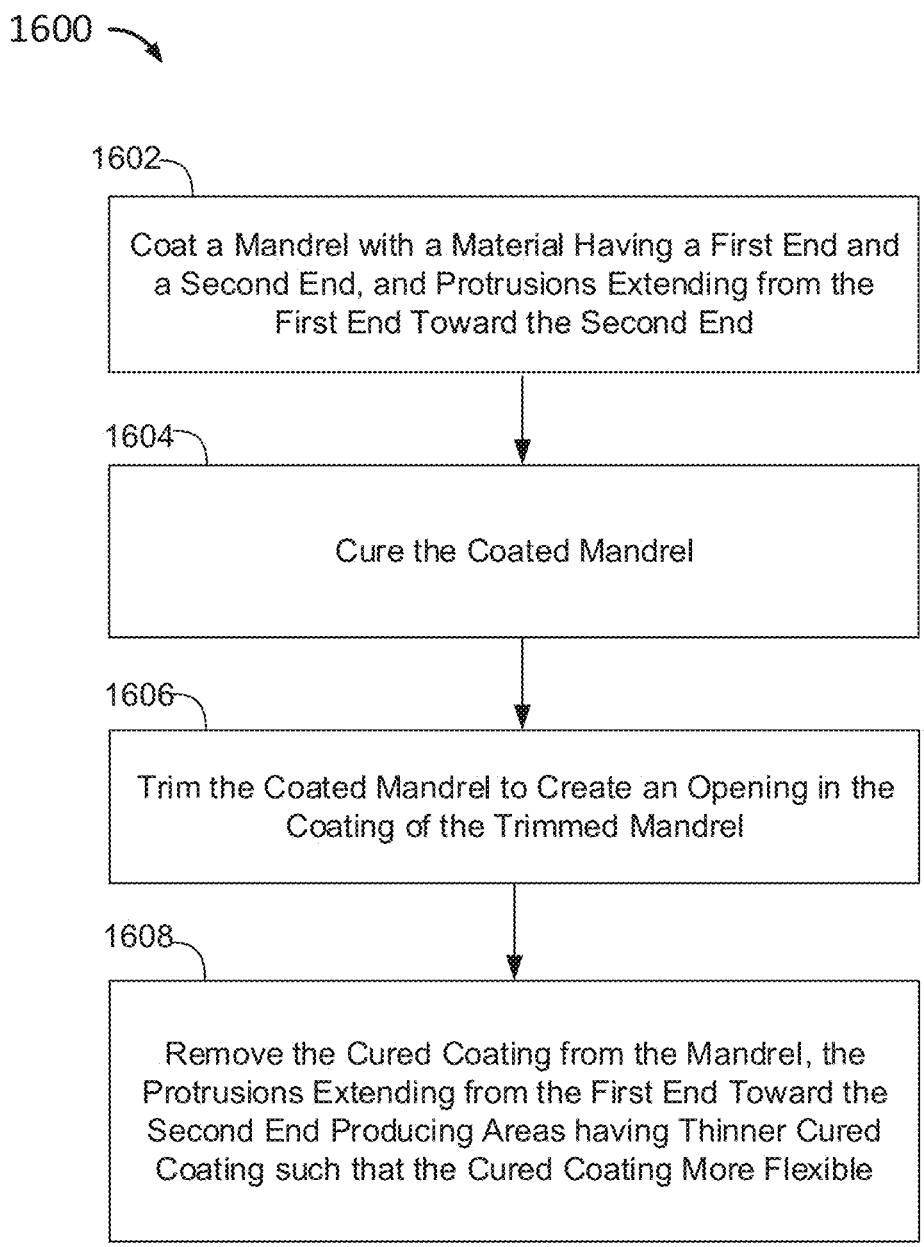
FIG. 16 shows a flow chart illustrating a method for manufacturing of a nasal cannula for respiratory therapy.

FIG. 16 shows a flow chart illustrating a method 1600 for manufacturing of a nasal cannula for respiratory therapy using a dip molding process. At step 1602, a mandrel is coated with a material. The mandrel has a first end and a second end and has protrusions extending from the first end toward the second end. The protrusions may be formed as protruding lines which may be broken lines or continuous. At step 1604, the coated mandrel is cured such that the material on the coated mandrel becomes solidified. At step 1606, the coated mandrel is trimmed to create an opening in the coating of the trimmed mandrel. The opening may be at the first end. At step 1608, the cured coating is removed from the mandrel. The protrusions extending from the first end toward the second end produce areas in the cured coating which have a smaller thickness than other regions, such that the coating is more flexible and able to be deformed by folding or bending in these areas.

In some implementations, the mandrel may not have protrusions on the surface. The mandrel may instead be shaped to form a nasal prong having the shape of FIGS. 6-13. In some implementations, the mandrel is shaped to have the geometric shape of the closed-configuration or the configuration which the prong assumes when the flow rate of the provided breathing gas is low. In some implementations, the mandrel has indentations or protrusions on the surface of the mandrel in order to form protrusions into a lumen of the nasal prong formed from the cured coating on the mandrel.

The method described with regard to FIG. 16 may be used in the production of any of the nasal cannulas described in FIGS. 1-3, and may be used to produce a nasal cannula having geometrically variable prongs as described in FIGS. 6-13. Further, the method can be utilized to produce nasal prongs having protrusions as described with regard to FIGS. 14 and 15.

Figure 17:
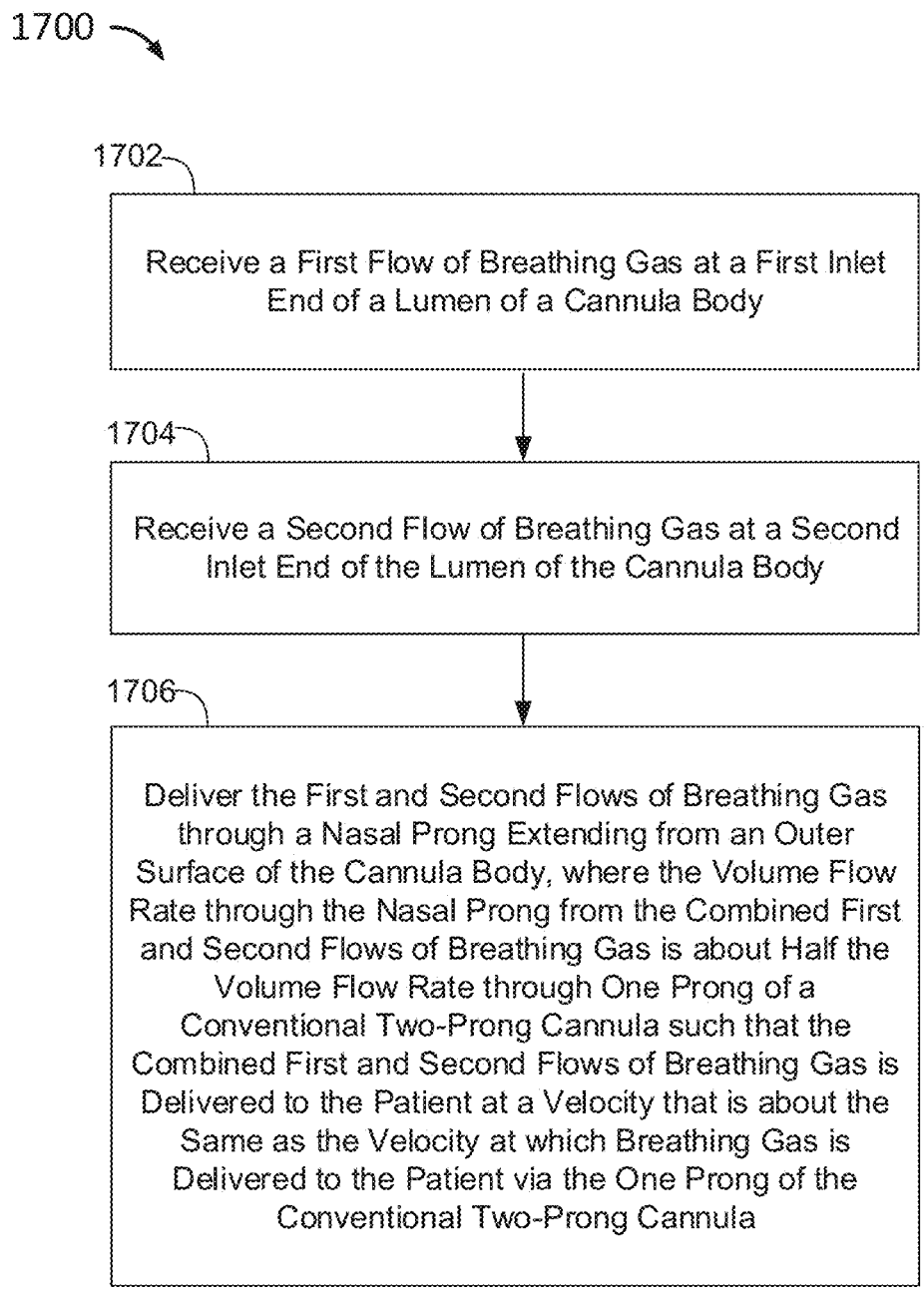
FIG. 17 shows a flow chart illustrating a method of providing respiratory therapy to a patient.

FIG. 17 shows a flow chart illustrating a method 1700 of providing respiratory therapy to a patient. At step 1702, a first flow of breathing gas is received at a first inlet end of a lumen of a cannula body. For example, the first flow of breathing gas can be received at a first inlet end 104 of cannula body 100 of FIG. 1. At step 1704, a second flow of breathing gas is received at a second inlet end of a lumen of a cannula body. For example, the second flow of breathing gas can be received at the second inlet end 106 of cannula body 100 of FIG. 1. At step 1706, the first and second flows of breathing gas are delivered through a nasal prong extending from an outer surface of the cannula body. For example, the first and second flows of breathing gas are delivered through nasal prong 112 in FIG. 1. The volume flow rate through the nasal prong from the combined first and second flows of breathing gas is about half of the volume flow rate through one prong of a conventional two-prong cannula. The combined first and second flows of breathing gas is delivered to a patient through the nasal prong at a velocity that is about the same as the velocity at which breathing gas is delivered to the patient via the one prong of the conventional two prong cannula.

For example, a flow rate of the breathing gas through a conventional two-prong cannula may be about 40 L/min (e.g., 35 L/min, 37 L/min, 39 L/min, 40 L/min, 41 L/min, 43 L/min, 45 L/min, or 50 L/min), and the flow rate of the breathing gas through the single prong may be about 20 L/min (e.g., 15 L/min, 17 L/min, 19 L/min, 20 L/min, 21 L/min, 23 L/min, or 25 L/min). For example, the velocity of the breathing gas may be about 48 m/s (e.g., 35 m/s, 40 m/s, 45 m/s, 50 m/s, 55 m/s). The flow rate of the breathing gas through the single prong may be about half of the flow rate through a conventional two-prong cannula. The velocity of the gas delivered to the patient may be maintained as compared to a conventional dual prong cannula, for example at about 48 m/s. As described above with regard to FIG. 6, variation of the geometry of the nasal prong such that the cross-sectional area of the lumen is changed with the flow rate of the gas enables the decrease in velocity with decreased flow rate to be minimized. Maintaining a high velocity of the gas provided to the patient provides effective flushing of the patient's airways, while improving patient comfort and efficiency of therapy. Decreased flow rate to the cannula can improve the battery life of breathing gas providing devices and relieves the need for wall-based breathing gas, while also decreasing the noise of the device. At the same time, effective therapy can be provided to patients to efficiently flush the patient's airways.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. The disclosed features may be implemented, in any combination and subcombination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A cannula for providing respiratory therapy to a patient, the cannula comprising:
   a first nasal prong having a proximal end attached to a cannula body, and a distal end for insertion into a nare of the patient; and
   the first nasal prong defining a lumen for a flow of breathing gas from a source of breathing gas to the nare of the patient;
   wherein the first nasal prong is configured to have a variable geometry such that a cross-sectional area of the lumen at the distal end of the first nasal prong varies with a flow rate of breathing gas and wherein the distal end of the first nasal prong is shaped as a dome having a plurality of slits, wherein at no flow through the first nasal prong the slits are configured to be closed and at a first flow rate through the first nasal prong the slits are configured to be open.

2. The cannula of claim 1, wherein the cross-sectional area of the lumen at the distal end of the first nasal prong is configured to increase with an increase in flow rate and decrease with a decrease in flow rate.

3. The cannula of claim 2, wherein the variation in cross-sectional area of the lumen is configured to minimize a reduction in flow velocity of breathing gas at low flow rates compared to the reduction in flow velocity of breathing gas flowing in a nasal prong having a constant cross-sectional area.

4. The cannula of claim 3, wherein the distal end of the first nasal prong is configured to change between a first expanded shape and a second folded shape, wherein a cross-sectional area of the second folded shape is smaller than a cross-sectional area of the first expanded shape.

5. The cannula of claim 4, wherein a flow velocity through the first nasal prong is the same when the distal end of the first nasal prong is in the first expanded shape as in the second folded shape.

6. The cannula of claim 5, wherein the distal end of the first nasal prong is configured to assume the first expanded shape at a first flow rate, and to assume the second folded shape at a second flow rate, wherein the first flow rate is greater than the second flow rate.

7. The cannula of claim 6, wherein the first expanded shape comprises one of: a regular polygon, a decagon, an octagon, or a hexagon at the first flow rate, and wherein, correspondingly, the second folded shape comprises any one of: a star having a number of points, a five-pointed star, a four-pointed star, or a three-pointed star, respectively, at the second flow rate.

8. The cannula of claim 7, wherein the distal end of the first cannula is further configured to assume a third folded shape at a third flow rate, where the third flow rate is less than the first or second flow rates, the third folded shape having a third cross-sectional area less than the second cross-sectional area.

9. The cannula of claim 4, wherein the first expanded shape comprises a circular cross-sectional shape at the first flow rate, the circular shape having a first distance extending between a first point and a second point opposite the first point on a circumference of the circular shape, and a second distance extending between a third point and a fourth point opposite the third point, wherein the third point is equidistant from the first point and the second point, and wherein at a first flow rate of breathing gas flow through the first nasal prong a first difference between the first distance and the second distance is less than a second difference between the first distance and the second distance at a second flow rate of breathing gas lower than the first flow rate.

10. The cannula of claim 9, wherein at the second flow rate, the cross-sectional shape of the distal end of the first nasal prong comprises any one of: an oval shape, a hippopede or pinched oval shape, a double-pointed teardrop shape and crescent/kidney shape.

11. The cannula of claim 1, wherein the first nasal prong includes a deformable nasal pillow extending from an external surface of the first nasal prong.

12. The cannula of claim 11, wherein the nasal pillow substantially circumscribes the first nasal prong, and wherein the nasal pillow is sized to occlude a space between the nare and the first nasal prong when the first nasal prong is positioned in the nare of the patient.

13. The cannula of claim 12, wherein the nasal pillow comprises a rounded dome extending from the external surface of the first nasal prong.

14. The cannula of claim 12, the cannula further comprising a second nasal prong, wherein the second nasal prong does not include material extending orthogonally from an external surface.

15. The cannula of claim 1, the cannula further comprising one or more internal protrusions positioned within the lumen of the first nasal prong.

16. The cannula of claim 15, wherein the one or more internal protrusions is shaped as a surface protruding from a sidewall within the lumen of the first nasal prong.

17. The cannula of claim 16, wherein the surface is angled from an axis collinear with a longitudinal axis extending from the proximal end to the distal end of the first nasal prong.

18. The cannula of claim 15, wherein the one or more internal protrusions positioned within the lumen of the first nasal prong minimizes a reduction in flow velocity of breathing gas at low flow rates compared to a nasal prong having a smooth lumen interior.

19. The cannula of claim 15, wherein the one or more internal protrusions is shaped as a chevron, the chevron including a point and two angled arms extending from the point, the point oriented toward the proximal end or the distal end of the first nasal prong.

* * * * *